US012186279B2

(12) United States Patent
Steinmetz et al.

(10) Patent No.: US 12,186,279 B2
(45) Date of Patent: *Jan. 7, 2025

(54) SUSTAINED RELEASE COWPEA MOSAIC VIRUS OR VIRUS-LIKE PAR

(56) References Cited

OTHER PUBLICATIONS

Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.
Aljabali, et al., "CPMV-DOX 1-15 Delivers", Molecular Pharmaceutics, vol. 10, No. 1, Jan. 7, 2013, pp. 3-10.
Applicant: Case Western Reserve University; "Cancer Immunotherapy Using Virus Particles"; European Patent Application No. 18764856.3 for Supplementary European Search Report dated Dec. 22, 2020; 8 pgs.
Applicant: Case Western Reserve University; "Cancer Immunotherapy Using Virus Particles"; Office Action, dated Aug. 4, 2020; 3 pgs.
Applicant: Case Western Reserve University; "Plant Virus Particles for Delivery of Antimitotic Agents"; Extended European Search Report; dated Aug. 17, 2020; 11 pgs.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Canan Uluog, et al.: "Intermediate dose of methotrexate toxicity in non-Hodgkin lymphoma", General Pharmacology, vol. 32, 1999, pp. 215-218, XP55711259.
European Search Report for Patent Application No. 15857504.3-1111/3215520, dated May 7, 2018.
Francisco, Joseph A., et al.; "cAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.
Gonzalez Maria Jet al: "Interaction of Cowpea Mosaic Virus (CPMV) Nanoparticles with Antigen Presenting Cells In Vitro and In Vivo", PLOS ONE, vol. 4, No. 11, Nov. 2009 (Nov. 2009), XP002780311, ISSN: 1932-6203.
Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.
Jantipa Jobsri et al., "Plant Virus Particles Carrying Tumour Antigen Activate TLR7 and Induce High Levels of Protective Anti body", PLOS ONE, vol. 10, No. 2, Jan. 1, 2015, pp. 1-16.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Lizotte, et al., "Plant-derived viral-like nanoparticle immunotherapy suppress development of metastatic lung cancer", Journal of Immunology, vol. 194, Issue 1 Supplement, May 2015; 4 pgs.
Miermont et al., "Cowpea Mosaic Virus Capsid: A promising Carrier for the Development of Carbohydrate Based Antitumor Vaccines", Chem. Eur. J., 2008, vol. 14, pp. 4939-4947.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Nicole F. Steinmetz; "Viral Nanoparticle Multimers"; U.S. Appl. No. 14/761,444, filed Jul. 16, 2015; Final Office Action dated Mar. 11, 2021; 11 pgs.
Office action for Chinese Patent Application No. 201580063662.6, dated Mar. 4, 2020.
Office action for European Patent Application No. 15 857 504.3-1111, dated Mar. 18, 2020.

Patrick H. Lizotte, "Novel approaches to targeting innate immunity for cancer immunotherapy", Proquest Dissertations Publishing, May 2015.
Pfizer Ltd .: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].
Sheen, et al., "Stimulating antitumor immunity with nanoparticles", Wiley Periodicals, Inc., vol. 6, Sep./Oct. 2014.
Shukla, et al., "The Impact of 1-15 Aspect Ratio on the Biodistribution and Tumor Homing of Rigid Soft-Matter Nanorods", Advanced Healthcare Materials, vol. 4, No. 6, Apr. 1, 2015.
Smyth etal. Treatment of rapidly growing K-BALB and CT26 mouse tumours using Semliki Forest virus and its derived vector. Gene Therapy (2005) 12, 147-159.
Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, KP55711263.
Wen, et al., "Interior Engineering of a Viral Nanoparticle and its Tumor Homing Properties" Macromolecules, vol. 13, No. 12, Dec. 2012.
Yildiz, et al., "Applications of Viral Nanoparticles in Medicine", Current Opinion Biotechnol, Dec. 2011 ; 22(6): pp. 901-908.
Plchova et al. Expression of Human papillomavirus 16 E7ggg oncoprotein on N- and C-terminus of Potato virus X coat protein in bacterial and plant cells. Protein Expression and Purification 77 {2011) 146-152.
Supplementary European Search Report for Patent Application No. 15857504.3-1111/3215520, dated May 28, 2018.
Office action for Japanese Patent Application No. 2017-524349, dated Jan. 31, 2020.
Dufes, C, et al. Dendrimers in Gene Delivery. Advanced Drug Delivery Reviews. 2005, vol. 3-11, 18-20. 26. 32-34 57; pp. 2177-2202. DOI:10.1016/j.addr.2005.09.017; p. 2178, Left Column, Section 1; p. 2186, Left Column, First Paragraph; p. 2191, Left Column, Third Paragraph to p. 2191, Right Column, First Paragraph, Section 3.3; p. 2192, Left Column, Second Paragraph; p. 2193, Right Column, Section 4.2, Third Paragraph.
Hauser. M, et al. pH-Triggered Release from Surface-Modified poly(lactic-co-glycolic acid) 4,5, 19,20 Nanoparticles. Beilstein J. Nanotechnol. 2015, vol. 6, pp. 2504-2512. doi:10.3762/bjnano.6.260; Abstract; p. 2506, Table 1; p. 2508, Right Column, Third Paragraph; p. 2509, Left Column, Figure 6.
Koudelka, KJ, et al. Virus-Based Nanoparticles As Versatile Nanomachines. Annu Rev Virol. 34 Nov. 2015, vol. 2, No. 1; pp. 379-401. doi: 10.1146/annurev-virology-100114-055141; Abstract; p. 4, Section of Virus-Based Nanoparticles in Therapeutic Interventions; p. 6, First Paragraph.
Steinmetz, NF. Viral Nanoparticles As Platforms for Next-Generation Therapeutics and 1-34 Imaging Devices. Nanomedicine. Oct. 1, 2011, vol. 6, No. 5. DOI: 10.1016/j.nano.2010.04.005; Abstract; p. 1, Section 1; p. 3, Section 3; p. 10, Figure 1; p. 5, Section 6, Third Paragraph to p. 6, First Paragraph; p. 10, Figure 1; p. 14, Figure 5.
Taki, A, et al. Small Wonders—The Use of Nanoparticles for Delivering Antigen. Vaccines. 1-34 2015, vol. 3; pp. 638-661. DOI:10.3390/vaccines3030638; Abstract; p. 640, Section 2; p. 641, Section 3; p. 642, Table 2, Third Paragraph; p. 644, First Paragraph; p. 645, Paragraph 3; p. 646, Second Paragraph; p. 647, Section 5.1, Figure 1 (a).
International Search Report for Application No. PCT/US17/43342, (2017).
European Application No. 17831976.0, Office Action dated Nov. 21, 2023.

* cited by examiner

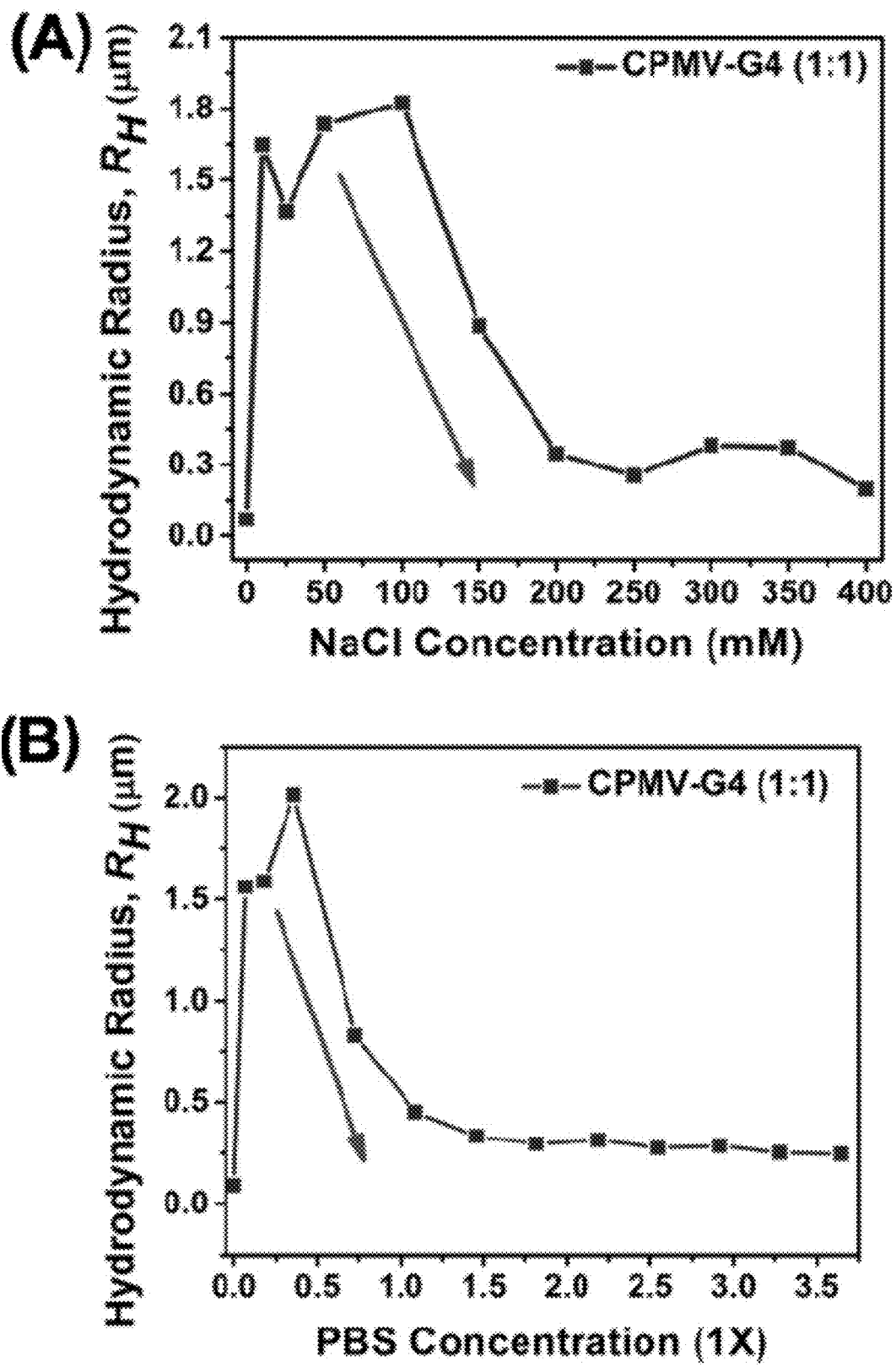
Figs. 1A-B

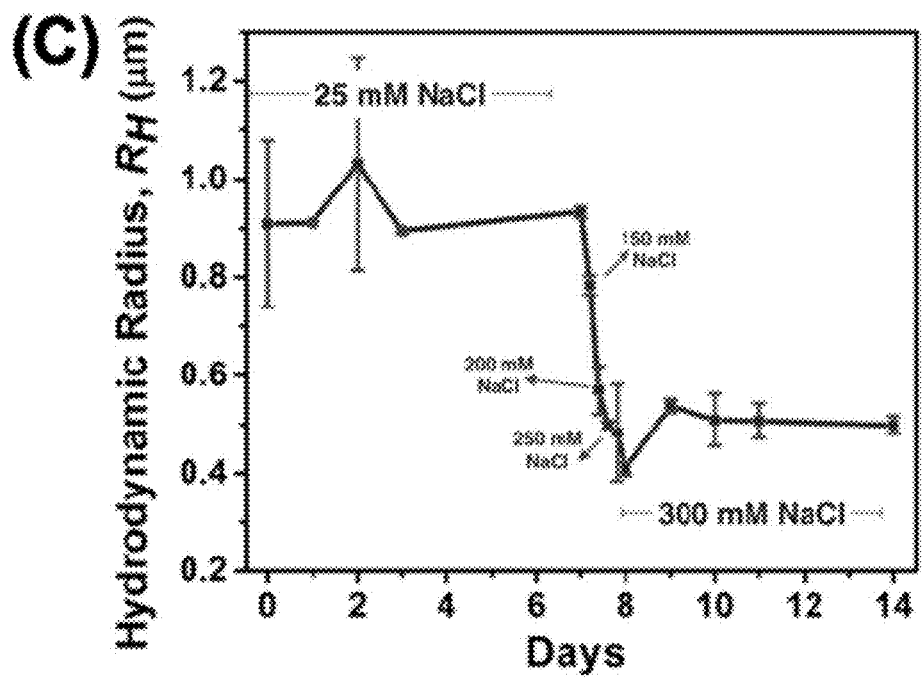
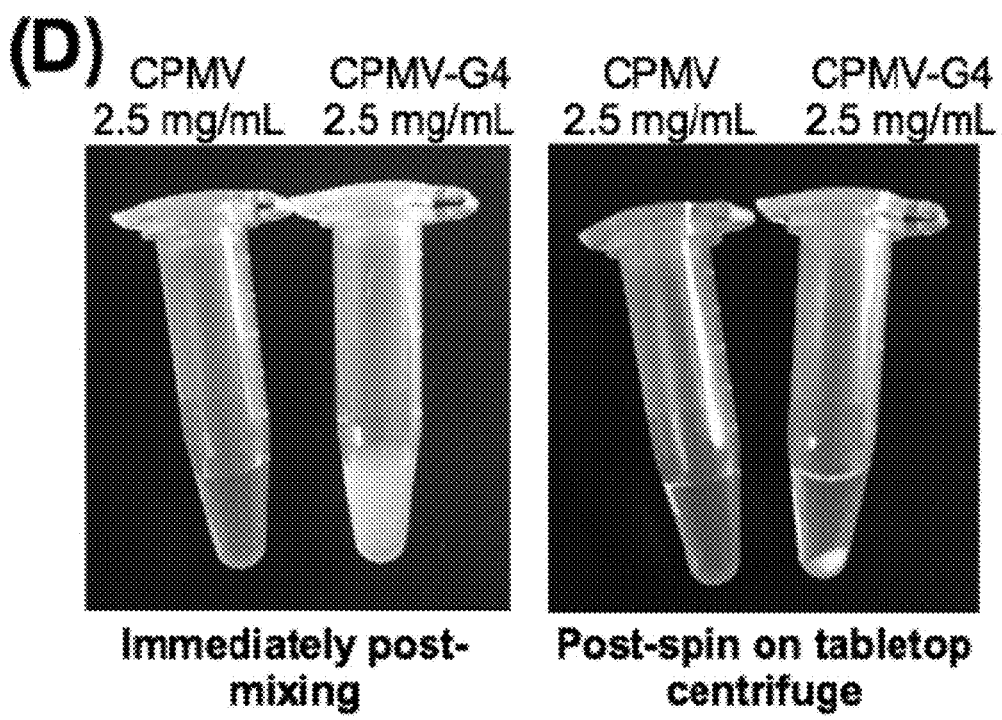
Figs. 1C-D

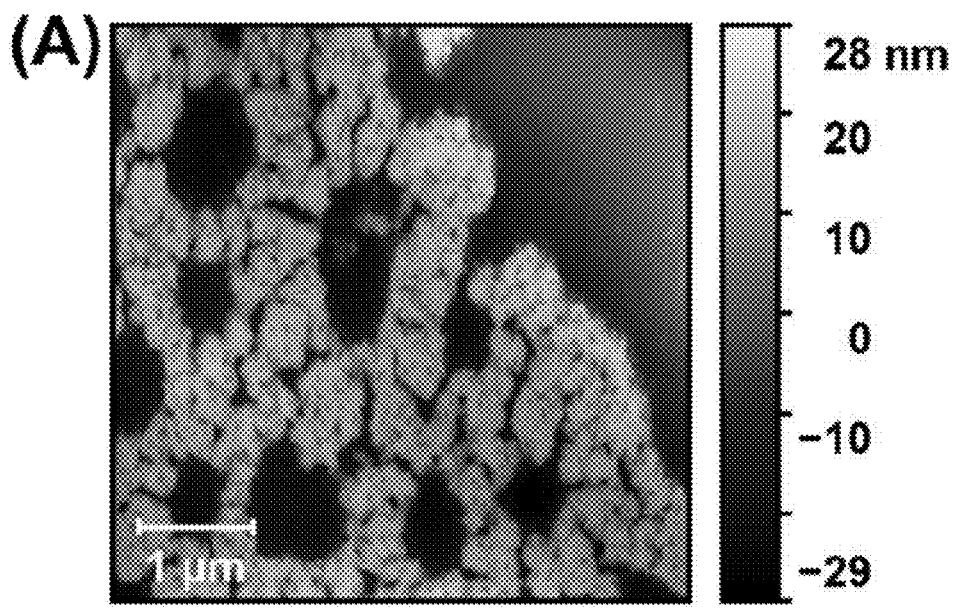
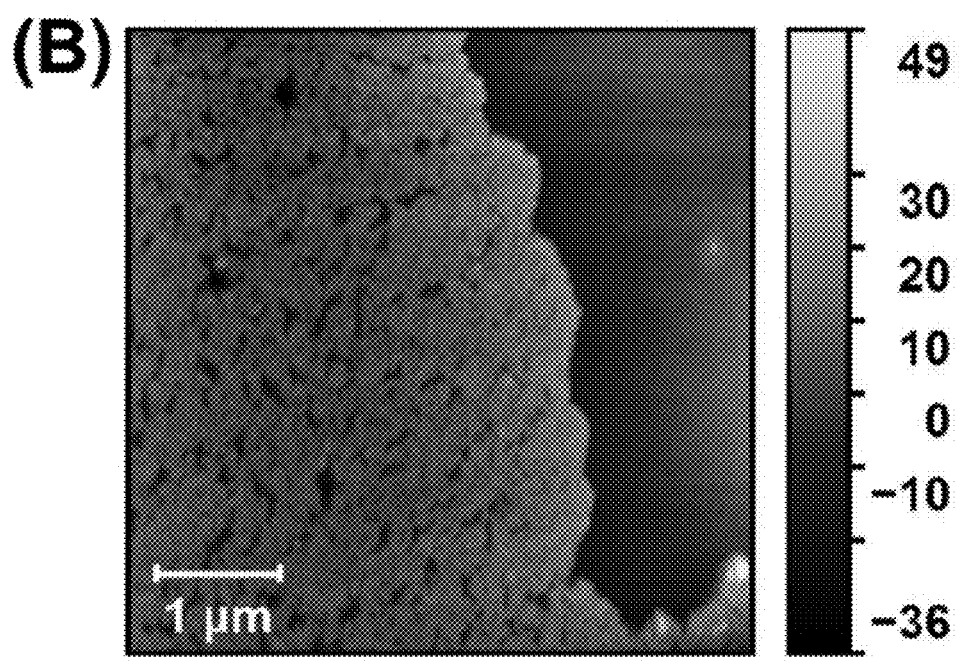
Figs. 2A-B

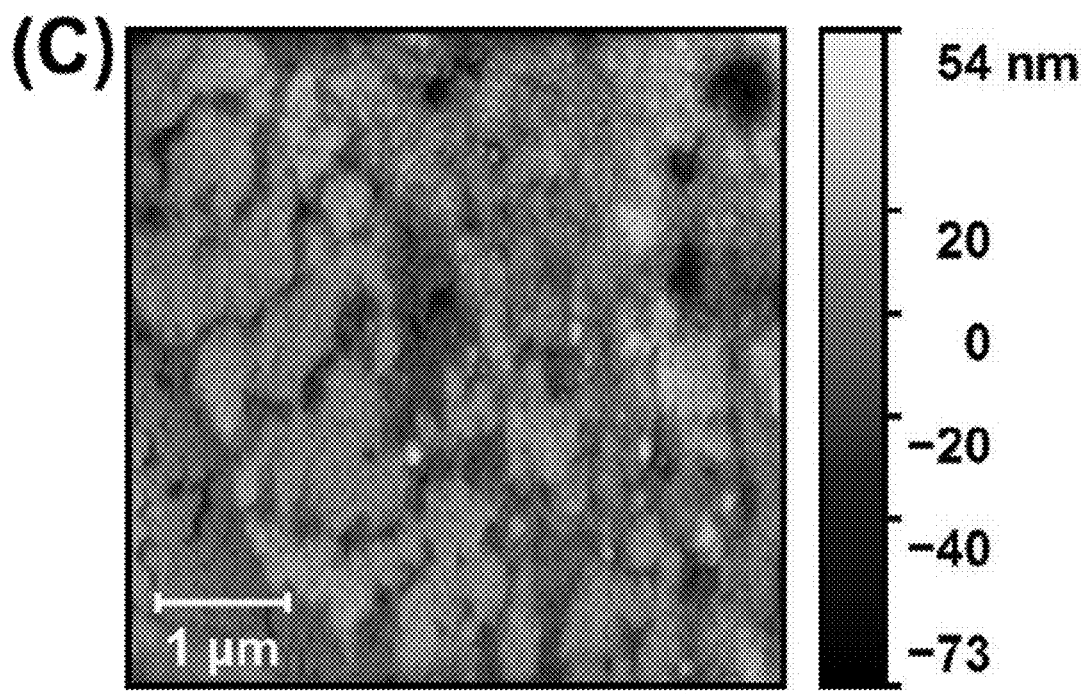
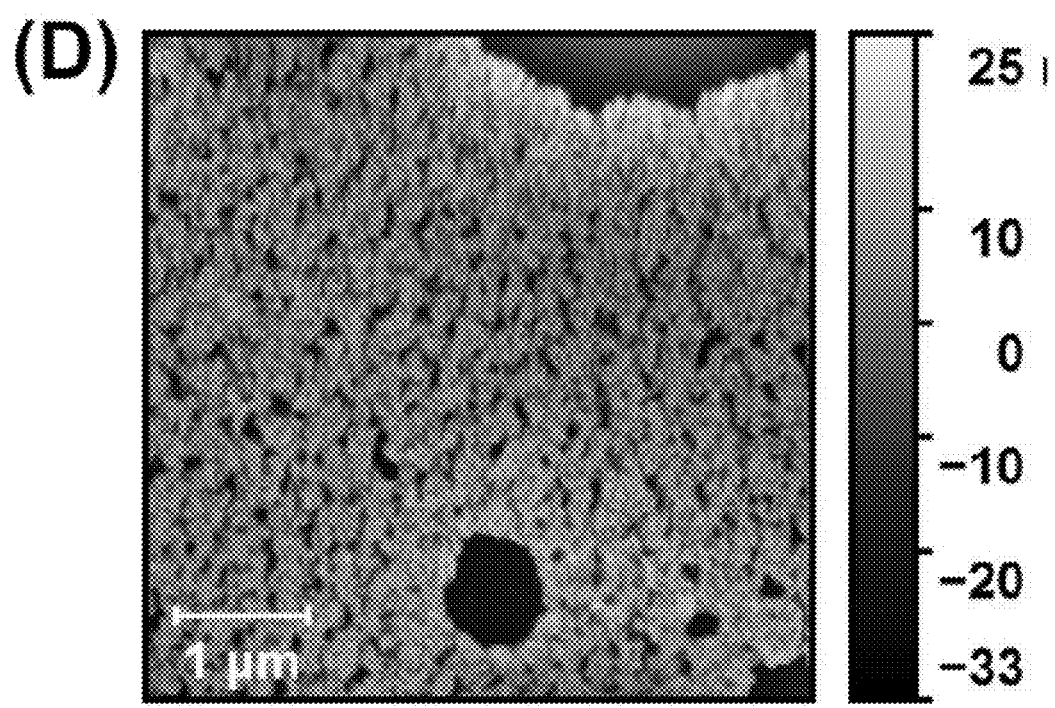
Figs. 2C-D

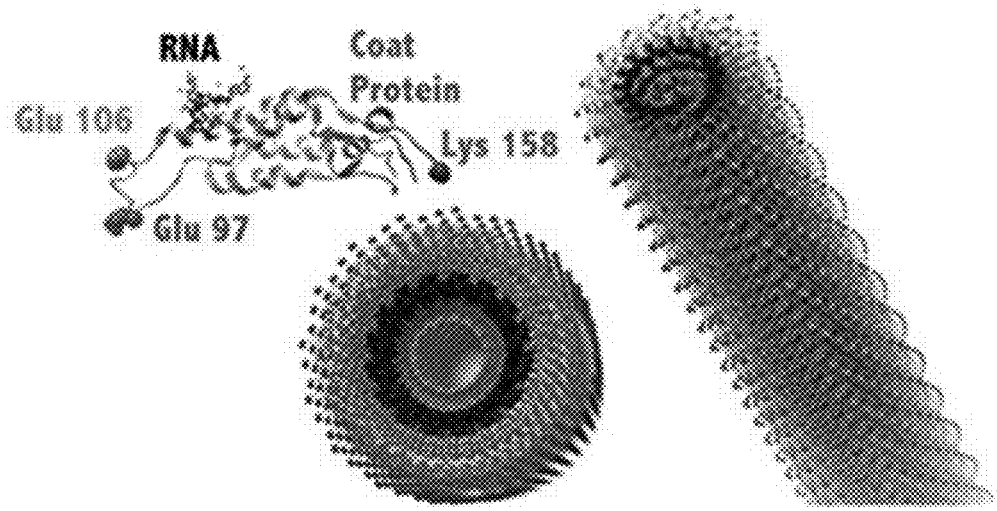
Fig. 6
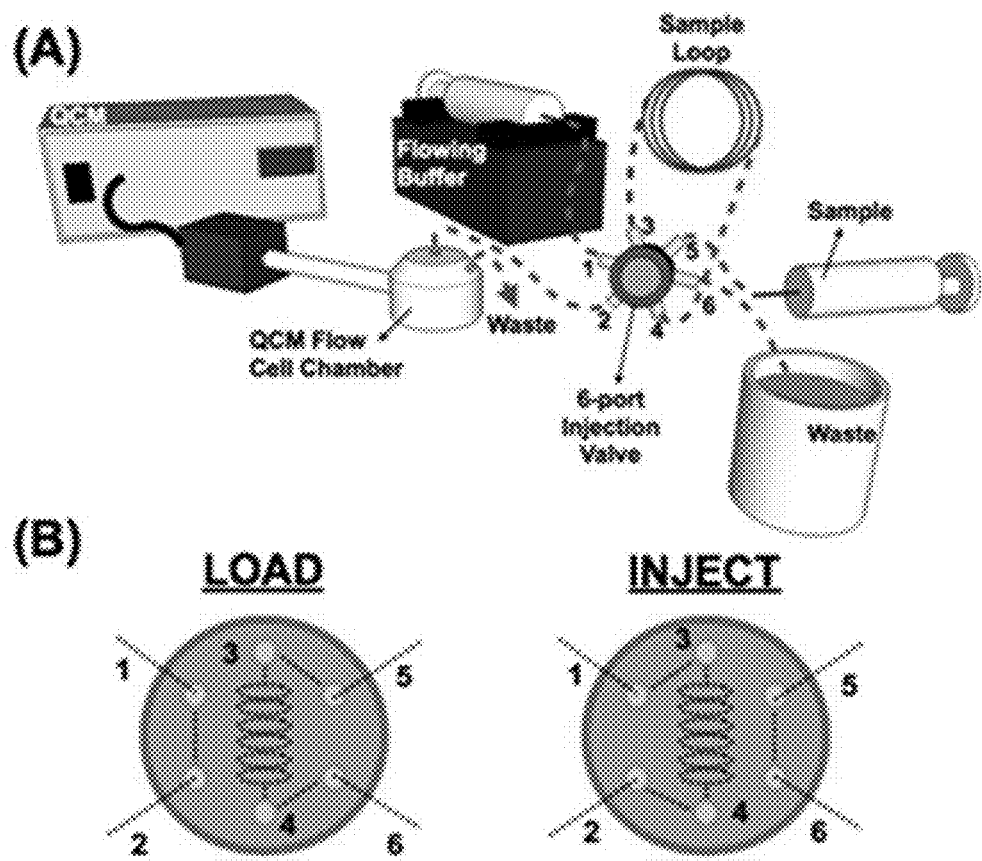
Figs. 7A-B

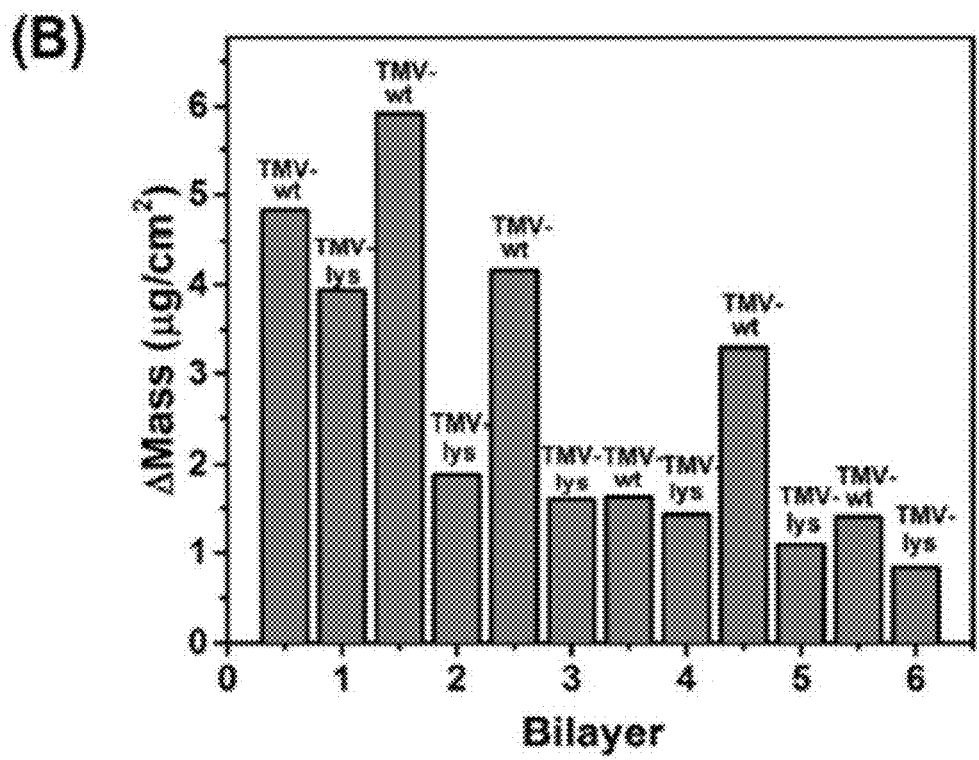
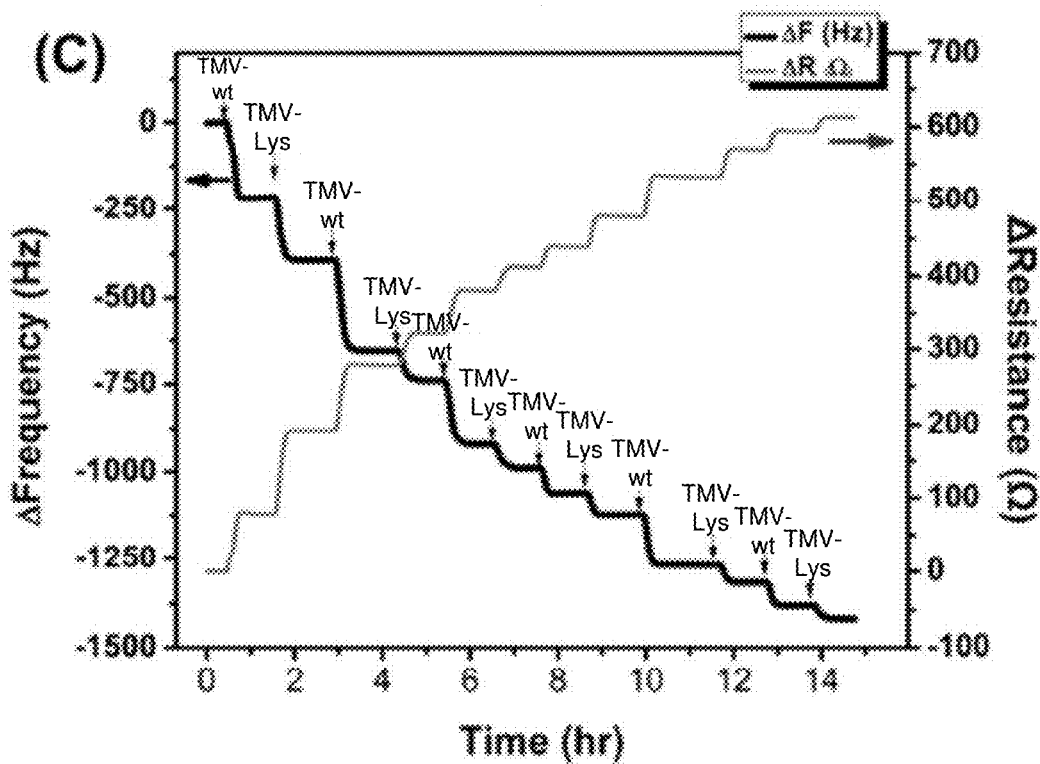
Figs. 9B-C

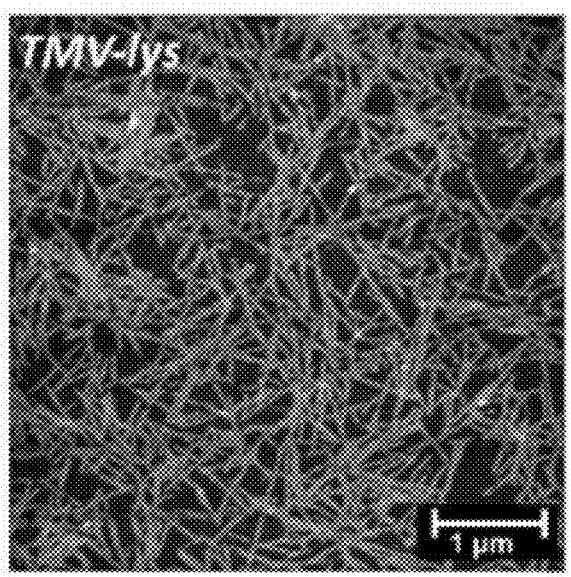
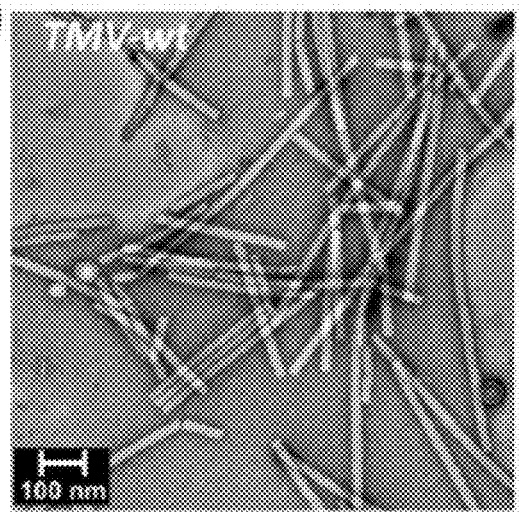
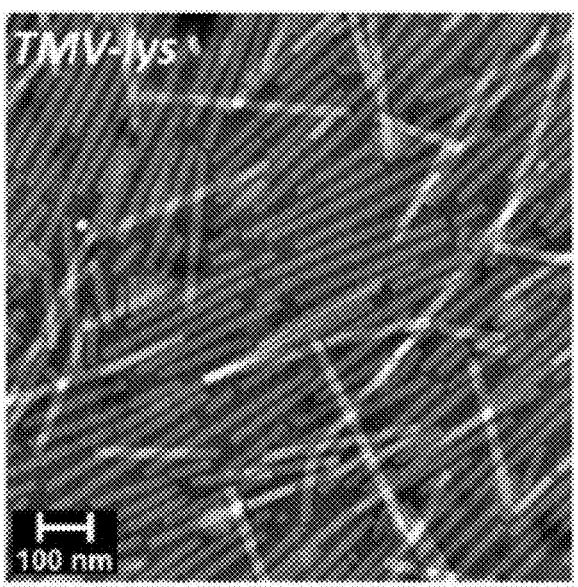
Figs. 10B-D

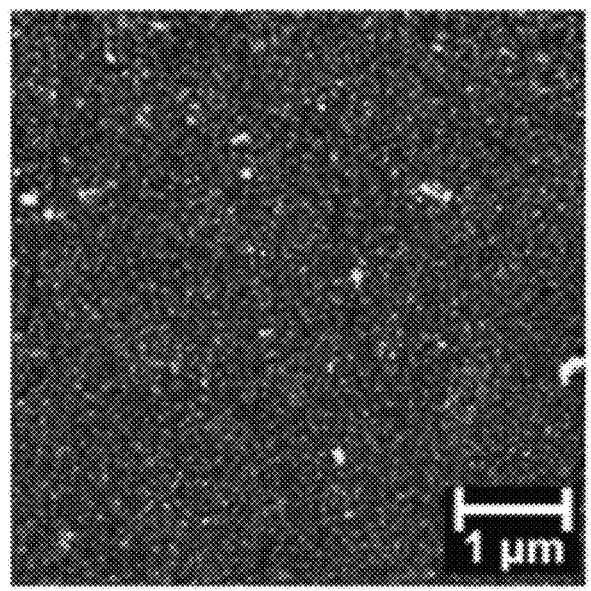
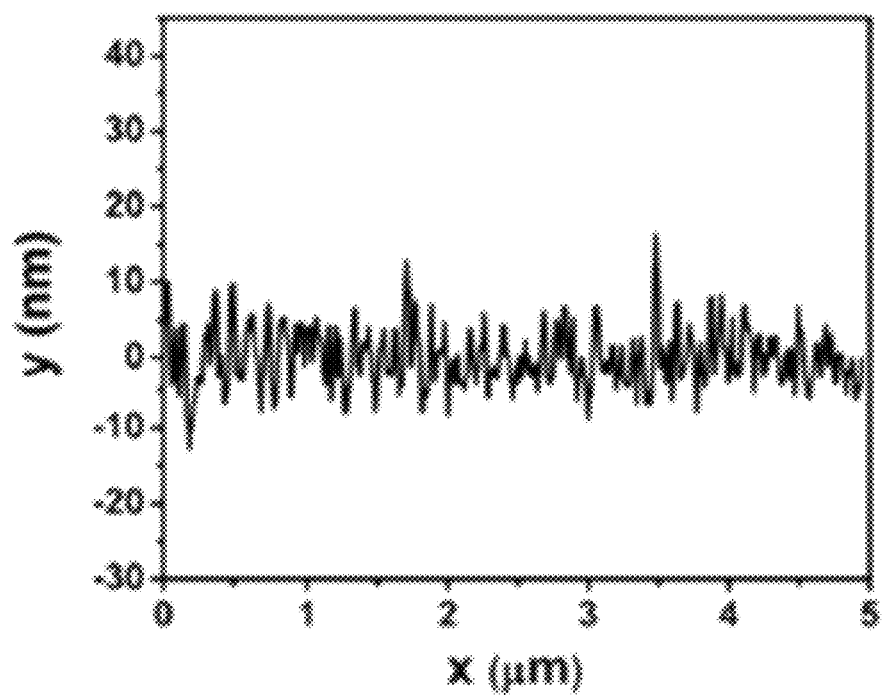
Fig. 11A

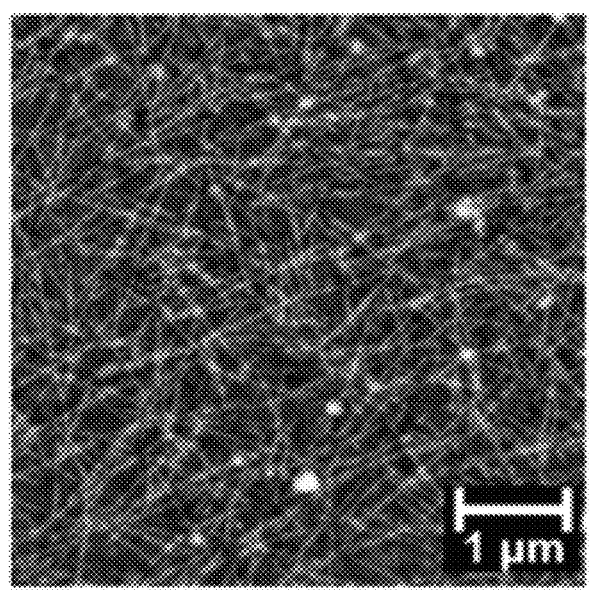
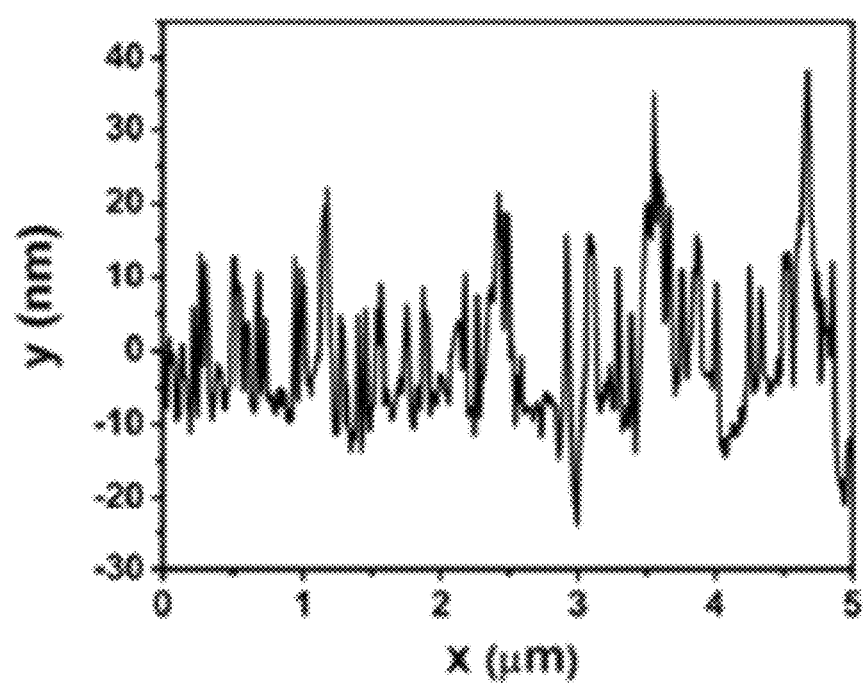
Fig. 11B

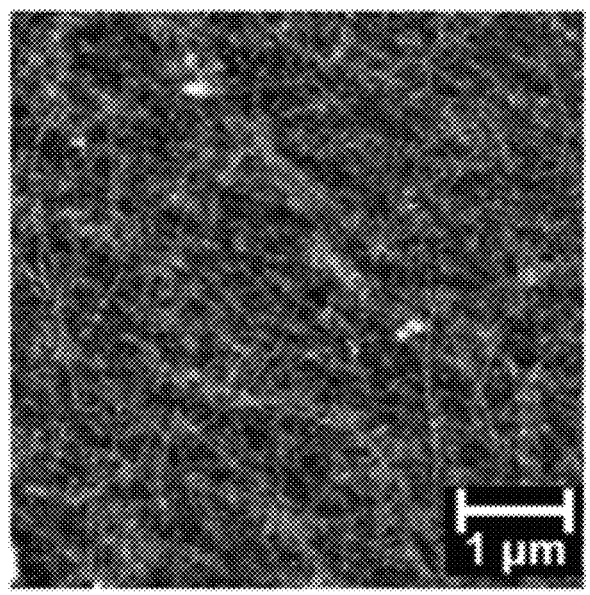
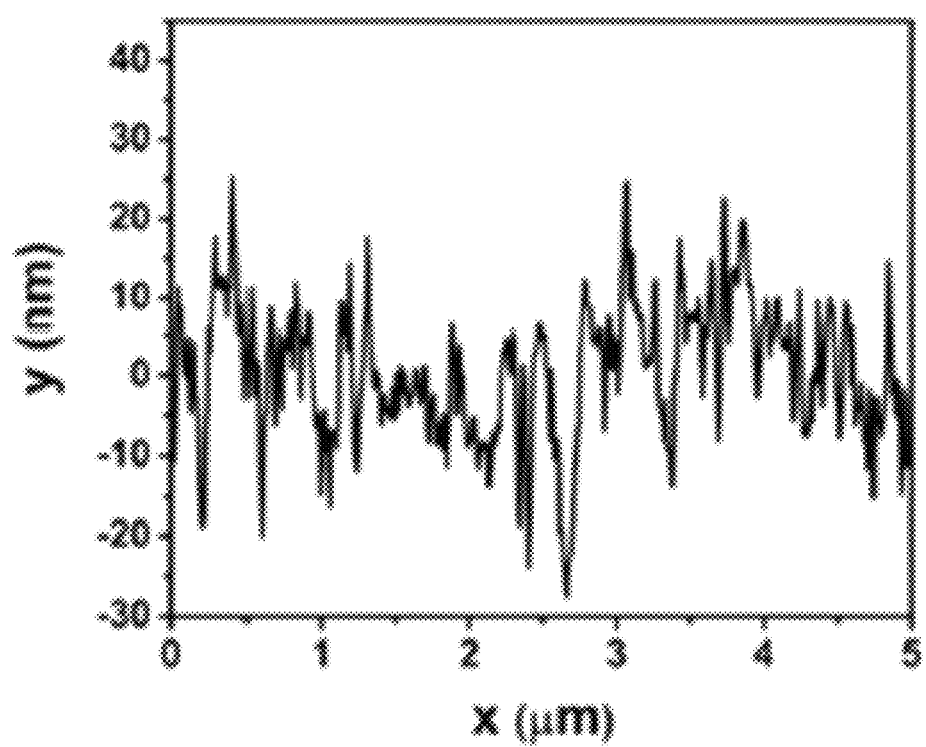
Fig. 11D

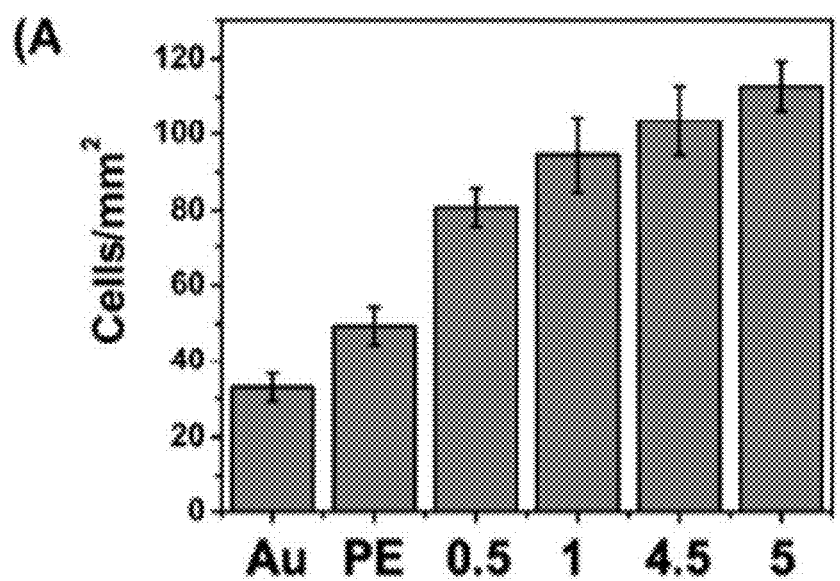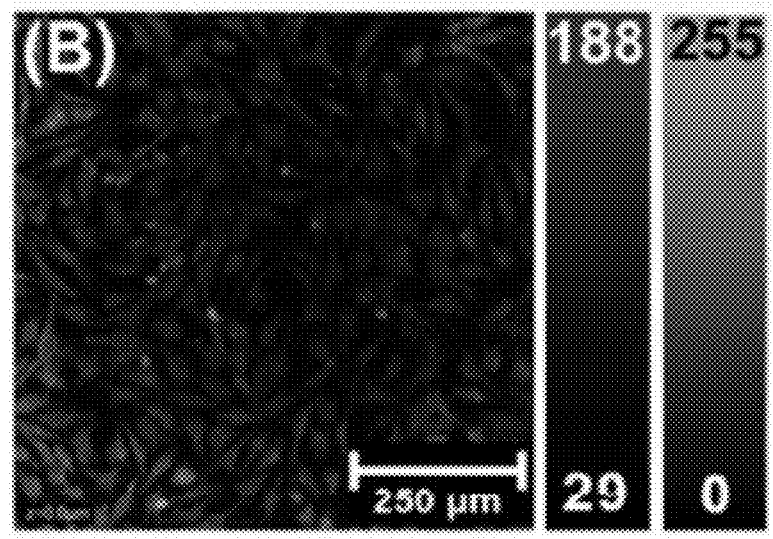
Figs. 12A-B

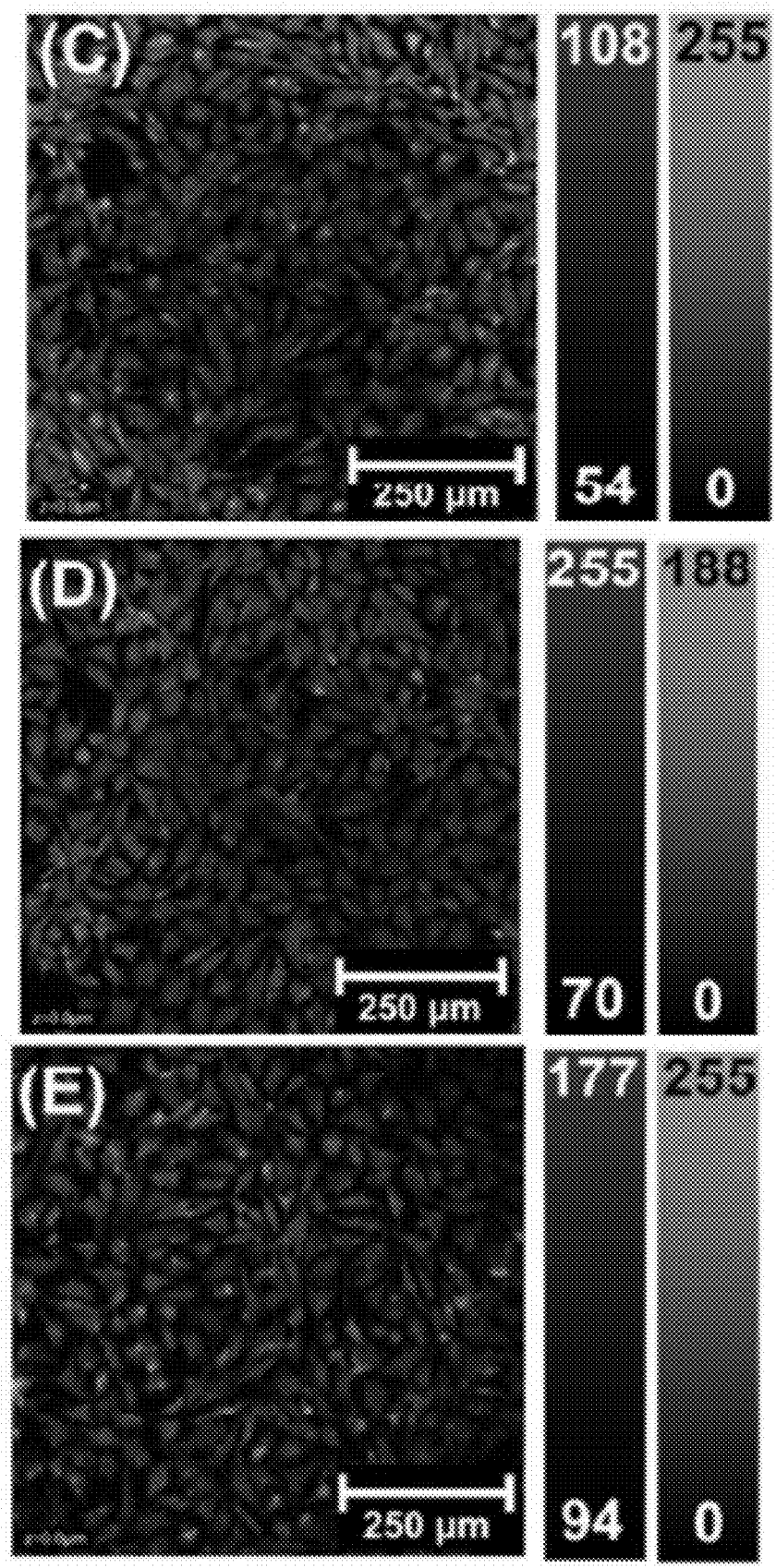
Figs. 12C-E

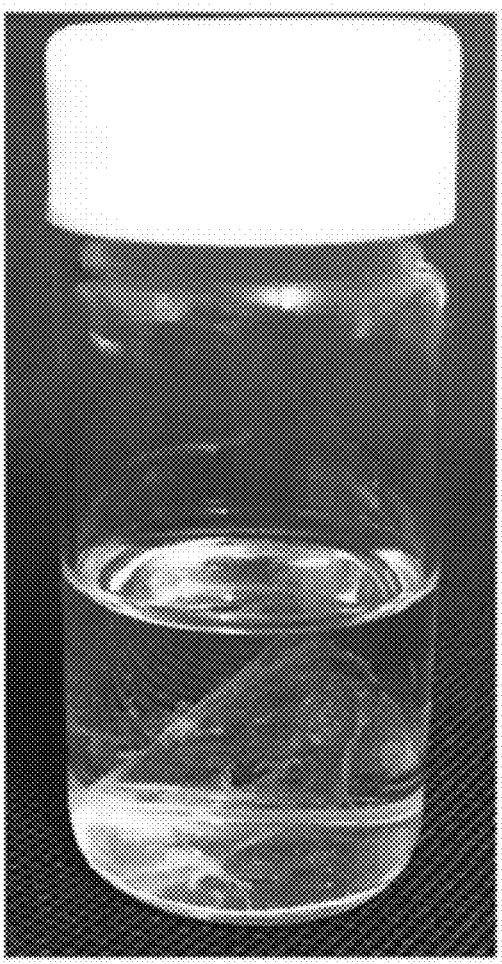
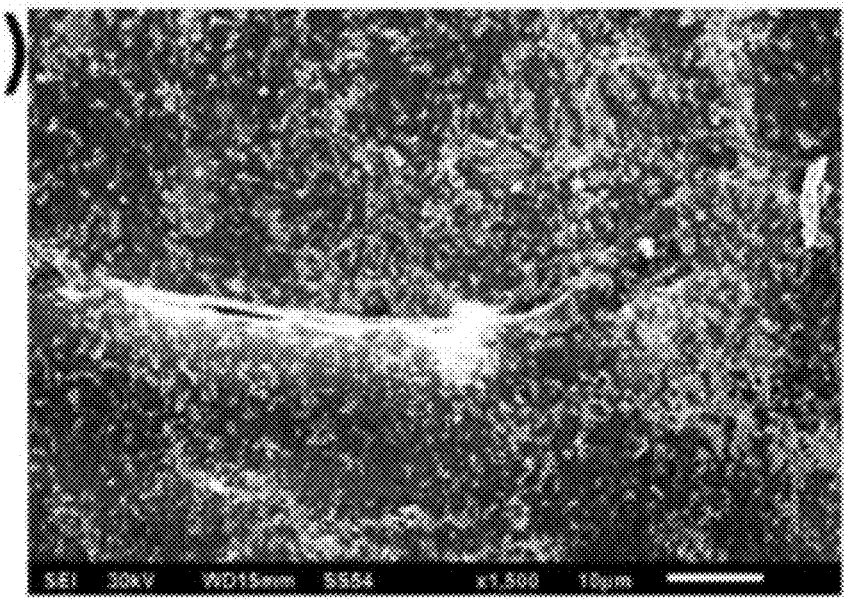
Figs. 13A-B

SUSTAINED RELEASE COWPEA MOSAIC VIRUS OR VIRUS-LIKE PARTICLE THERAPEUTIC CONSTRUCTS FOR THE TREATMENT OF CANCER

RELATED APPLICATION

This application claims priority to U.S. Provisional Application Ser. No. 62/364,949, filed Jul. 21, 2016, all of which are incorporated herein by reference.

GOVERNMENT FUNDING

This invention was made with government support under 1333651 awarded by the National Science Foundation and DE-SC0008068 awarded by the Department of Energy. The government has certain rights in the invention.

BACKGROUND

Research into nanoparticles as cancer therapies has largely focused on them as a delivery platform. Nanoparticles can be loaded with tumor-associated antigen and immune agonists for the stimulation of anti-tumor immunity and/or loaded with pre-existing conventional chemotherapeutic drugs for delivery to tumors as a means to reduce toxicity. However, the tendency of nanoparticles to interact with and to be ingested by innate immune cells gives them potential as immunostimulatory, immunoregulatory and immunostimulatory agents if they modulate the characteristics of the ingesting innate immune population.

Virus-like particles (VLPs) refer to the spontaneous organization of coat proteins into the three dimensional capsid structure of a particular virus. Like active viruses, these particles are in the 20-500 nm size range, but they are devoid of the virus nucleic acid. VLPs have already been deployed as antigen components of antiviral vaccines against infectious counterpart viruses hepatitis B (Halperin et al., Vaccine, 30(15):2556-63 (2012)) and human papilloma virus (Moreira et al., Hum Vaccin., 7(7):768-75 (2011)). By preventing infection with viruses that cause cancer, vaccines utilizing VLPs are currently contributing to reductions in cancer incidence.

Recent studies have demonstrated that VLP therapeutic efficacy extends beyond the specific antigen array that they carry and that they may possess inherent immunogenic properties that can stimulate immune responses against infectious agents that do not carry any antigen included in the VLP. Rynda-Apple et al., Nanomed., 9(12):1857-68 (2014)). VLPs have shown the ability to induce protective immune responses in the respiratory tract in mouse models of infectious diseases of the lungs. VLP treatment protected mice from bacterial pneumonia caused by methicillin-resistant *Staphylococcus aureus* (MRSA) (Rynda-Apple et al., Am J Pathol., 181(1):196-210 (2012)) and *Coxiella burnetii* (Wiley et al., PLoS ONE., 4(9):e7142 (2009)). VLPs have also been shown to protect mice in various influenza models. Patterson et al., ACS Nano., 7(4):3036-44 (2013); Richert et al., Eur J Immunol., 44(2):397-408 (2014). Protective immunity in these models was associated with recruitment, activation, and increased antigen-processing capabilities, formation of inducible bronchus-associated lymphoid tissue (iBALTs), and stimulation of $CD4^+$ T and B lymphocytes and $CD8^+$ T cells.

SUMMARY

Embodiments described herein relate to a nanoparticle construct that includes a plurality of plant virus or virus-like particles electrostatically coupled to a plurality of nanoparticles having a different surface charge than the plant virus or virus-like particles. The nanoparticle construct can upon delivery and/or administration to a subject, such as in situ delivery and/or administration, provide a sustained and/or controlled release of the plant virus or virus-like particles and/or nanoparticles to the cells or tissue. The nanoparticle construct can also serve as a substrate for the incorporation and/or attachment of at least one cargo agent, bioactive agent, and/or cell.

In some embodiments, the nanoparticle construct can form macro- or micro-scaffold that can be readily delivered to a subject to provide controlled and/or sustained release of the plant virus or virus-like particles and/or nanoparticles as well as the cargo agents and/or bioactive agents coupled to and/or loaded on the construct to cells and/or tissue of a subject. The nanoparticle construct can be injected or implanted in a minimally invasive fashion in a subject in need thereof to treat diseases (e.g., cancer) and/or disorders in the subject.

In some embodiments, the nanoparticles electrostatically coupled to the plant virus or virus-like particles can include at least one of virus or virus-like particles, dendrimers, metallic particles, inorganic particles, polymer particles, or liposomes that have a different surface charge than the plant virus or virus-like particles.

In some embodiments, the nanoparticle construct can be in the form of a micro-aggregate that includes a plurality of the electrostatically coupled dendrimers and the plant virus or virus-like particles. Micro-aggregates of the electrostatically coupled dendrimers and the plant virus or virus-like particles can be readily injected in a subject to be treated.

In some embodiments, micro-aggregates of the electrostatically coupled dendrimers and the plant virus or virus-like particles can have diameters large enough to prevent passive diffusion of the micro-aggregates across blood vessels following intraperitoneal injection into a subject thus requiring disassembly or lymphatic drainage for eventual clearance from the subject. For example, micro-aggregates of the electrostatically coupled dendrimers and the plant virus or virus-like particles can have an average hydrodynamic radius of about 100 nm to about two microns.

In some embodiments, micro-aggregates of the electrostatically coupled dendrimers and the plant virus or virus-like particles can be assembled in aqueous solutions with salt concentrations up to about 100 nM. Upon administration to a subject the micro-aggregates can gradually disassemble in a sustained manner at physiological salt concentrations over a defined period the time, such as about 1 day, 2 days, 3 days, 4 days, 5 days, 6 days, 1 week, 2 weeks or more.

In some embodiments, the plant virus or virus-like particle used for the nanoparticle construct can be a plant picornavirus or a filamentous plant virus or virus-like particle. The plant virus or virus-like particle can be of the *Secoaviridoe* genus or Alphafexiviridae family. For example, the plant virus or virus-like particle can be a cowpea mosaic virus-like particle or potato virus X virus-like particle. In other embodiments, the plant virus particle or virus-like particle can be a rod-shaped virus particle. The rod-shaped virus can be a tobacco mosaic virus. The dendrimer can a G3-G10 dendrimer, such as a G4-G6 dendrimer.

In other embodiments, the nanoparticle construct can have a three-dimensional periodic nanoscale architecture, such as a hierarchical complex with defined alternating electrostatically coupled layers of the plant virus or virus-like particles and the nanoparticles. The nanoparticles used to form the electrostatically coupled layers can include plant virus or virus-like particles that have differing surface charges. For example, tobacco mosaic virus (TMV) can be genetically engineered to display a corona of lysine residues on its solvent exposed surface that alters the surface charge of the TMV sufficiently to allow layer by layer electrostatic coupling of the TMV to TMV-lys.

Other embodiments described herein relate to methods of treating cancer in a subject in need thereof by administering in situ to cancer of the subject a therapeutically effective amount of a nanoparticle construct. The nanoparticle construct can include a plurality of plant virus or virus-like particles electrostatically coupled to a plurality of nanoparticles having a different surface charge than the plant virus or virus-like particles. The virus or virus-like particle can be nonreplicating and noninfectious in the subject to avoid infection of the subject. In some embodiments, the in situ administration of the nanoparticle construct can be proximal to a tumor in the subject or directly to the tumor site to provide a high local concentration and sustained and/or controlled release of the plant virus or virus-like particle in the tumor microenvironment. The method represents a type of in situ vaccination, in which application of an immunostimulatory reagent directly to the tumor modifies the tumor microenvironment so that the immune system is able to respond to the tumor.

BRIEF DESCRIPTION OF THE FIGURES

FIGS. 1(A-C) illustrate DLS measurements for the assembly and disassembly of CPMV and PAMAM-G4 dendrimer in (A) increasing NaCl and (B) PBS concentrations. (C) Stability study for the CPMV-G4 assembly, wherein the ionic strength was initially fixed at 25 mM NaCl for 1 week, gradually increased, and was kept at 300 mM NaCl for another 7 days. (D) Aggregates of high concentration (2.5 mg/mL) CPMV and PAMAM-G4 in 25 mM NaCl.

FIGS. 2(A-D) illustrate topographical tapping-mode AFM images of (A) 0.15 mg/mL CPMV and 0.15 mg/mL CPMV-G4 (1:1) in (B) 0 mM, (C) 50 mM, and (D) 150 mM NaCl, which were dropcasted on a freshly cleaved mica surface.

FIG. 6 illustrates the structure of the TMV-lys coat protein and the assembled hollow various nanotube.

FIGS. 7(A-B) are a (A) schematic layout of the quartz crystal microbalance (QCM)-flow injection analysis (FIA) setup. (B) Illustration of the port connections within the 6-port injection valve that facilitated the noiseless introduction of the virus nanoparticles on the QCM crystal surface.

FIGS. 12(A-E) illustrate (A) summary of cells that adhered on the blank and PE-modifed substrates and the multilayer viral scaffolds. Fluorescence micrographs (scale bar=250 µm) of NIH-3T3 fibroblasts that remain attached on (B) (TMV-wt/TMV-lys)0.5, (C) (TMV-wt/TMV-lys)1, (D) (TMV-wt/TMV-lys)4.5, and (E) (TMV-wt/TMV-lys)5.

DETAILED DESCRIPTION

Figure 3:
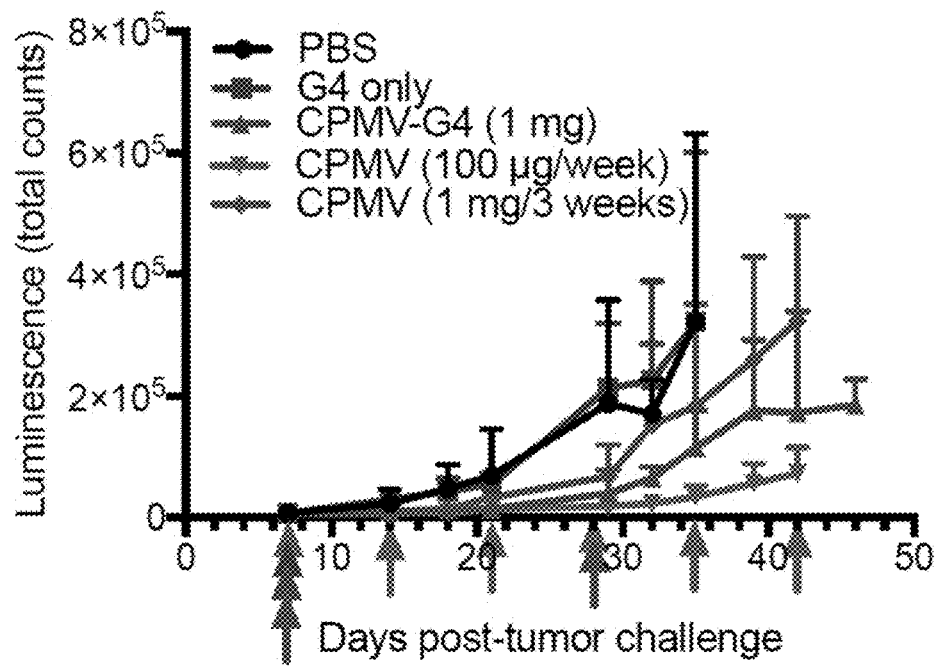
FIG. 3 illustrates growth of ovarian cancer cells in the intraperitoneal space. Treatment was injected intraperitoneally and initiated seven days following injection of 2 million luciferase-positive ID8-Def29/Vegf-A cells. Injection of each treatment group is indicated with a color-coordinated arrow. PBS was also injected weekly. Total bioluminescence measured in intraperitoneal space.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

The term "agent" refers to a chemical compound, a mixture of chemical compounds, a biological macromolecule, or an extract made from biological materials.

The term "bioactive agent" can refer to any agent capable of promoting a biological effect, e.g., alters or modulates a biological function of a physiological target substance. By "alters" or "modulates a biological function" herein is meant that the physiological target undergoes a change in either the quality or quantity of its biological activity; this includes increases or decreases in activity. Thus, bioactive agents include a wide variety of drugs, including antagonists, for example enzyme inhibitors, and agonists, for example a transcription factor which results in an increase in the expression of a desirable gene product (although as will be appreciated by those in the art, antagonistic transcription factors may also be used), are all included.

In addition, a "bioactive agent" includes those agents capable of direct toxicity and/or capable of inducing toxicity towards healthy and/or unhealthy cells in the body. Also, the bioactive agent may be capable of inducing and/or priming the immune system against potential pathogens. A number of mechanisms are possible including without limitation, (i) a radioisotope linked to a protein as is the case with a radiolabled protein, (ii) an antibody linked to an enzyme that metabolizes a substance, such as a prodrug, thus rendering it active in vivo, (iii) an antibody linked to a small molecule therapeutic agent, (iv) a radioisotope, (v) a carbohydrate, (vi) a lipid, (vii) a thermal ablation agent, (viii) a photosensitizing agent, and (ix) a vaccine agent.

The term "cargo molecule" or "cargo agent", refers to a small organic or inorganic bioactive agent, such as a drug or imaging agent, that can be associated with a virus particle multimer in order to confer an additional function on the virus particle multimer.

The term "imaging agent" can refer to a biological or chemical moiety capable being linked and/or conjugated directly or indirectly to nanoparticle constructs described herein and that may be used to detect, image, and/or monitor the presence and/or progression of a cell cycle, cell function/physiology, condition, pathological disorder and/or disease.

The terms "peptide," "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. A protein may be a receptor or a non-receptor. "Apa" is aminopentanoic acid.

A "nucleic acid" refers to a polynucleotide and includes polyribonucleotides and polydeoxyribonucleotides.

"Treating" treating refers to ameliorating the effects of, or delaying, halting or reversing the progress of a disease or disorder. The word encompasses reducing the severity of a symptom of a disease or disorder and/or the frequency of a symptom of a disease or disorder.

A "subject" can be a human or non-human animal Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to provide effective imaging or treatment in a subject, depending on the compound being used. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

Embodiments described herein relate to nanoparticle constructs that include a plurality of plant virus or virus-like particles electrostatically coupled to a plurality of nanoparticles having a different surface charge than the plant virus or virus-like particles. The nanoparticle constructs can upon delivery and/or administration to a subject, such as in situ delivery and/or administration, provide a sustained release of the plant virus or virus-like particles and/or nanoparticles to cells or tissue of the subject.

In some embodiments, the nanoparticle constructs can also serves as a substrate for the incorporation and/or attachment of at least one cargo agent, bioactive agent and/or cell. The nanoparticle construct can form macro- or micro-scaffold that can be readily delivered to a subject to provide controlled and/or sustained release of the plant virus or virus-like particles and/or nanoparticles as well as the cargo agents and/or bioactive agents coupled to and/or loaded on the construct to cells and/or tissue of a subject. The nanoparticle construct can be injected or implanted in a minimally invasive fashion in a subject in need thereof to treat diseases (e.g., cancer) and/or disorders in the subject.

Plant virus particles that are electrostatically coupled to the nanoparticles can be readily cultivated, and are unlikely to cause infection when used in vivo in a subject. Plant virus particles are categorized based on their source and structure. In various embodiments, the plant virus particles having an icosahedral, filamentous, or rod-shaped structure can be used. The plant virus particles can be non-enveloped virus particles. Examples of icosahedral plant viruses include cowpea mosaic virus, brome mosaic virus, cowpea chlorotic mottle virus, etc.

In some embodiments, the plant virus or virus-like particles can be an icosahedral plant virus or virus-like particle. Examples of icosahedral plant viruses include the virus families Geminiviridae, Luteoviridae, Bromoviridae, Phycodnaviridae, and Picornaviridae. In some embodiments, the icosahedral plan virus is from the family Picornaviridae. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily. Examples of viruses from the Comovirinae subfamily include Cowpea mosaic virus, Broad bean wilt virus 1, and Tobacco ringspot virus. In a further embodiment, the virus particles are from the Genus *Comovirus*. An example of a *Comovirus* is the cowpea mosaic virus particles.

In other embodiments, the plant virus or virus-like particle is a filamentous plant virus. Filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm.

In some embodiments, the filamentous plant virus belongs to a specific virus family, genus, or species. For example, in some embodiments, the filamentous plant virus belongs to the Alphaflexiviridae family. The Alphaflexiviridae family includes the genus *Allexivirus, Botrexvirus, Lolavirus, Mandarivirus, Potexvirus*, and *Sclerodamavirus*. In some embodiments, the filamentous plant virus belongs to the genus *Potexvirus*. In further embodiments, the filamentous plant virus belongs to the Potato Virus X species.

In other embodiments, the plant virus or virus-like particle can be based on a rod-shaped plant virus or virus-like particle. A rod-shaped plant virus is a virus that primarily infects plants, is non-enveloped, and is shaped as a rigid helical rod with a helical symmetry. Rod shaped viruses also include a central hollow canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, in some embodiments, the rod-shaped plant virus belongs to the Virgaviridae family. The Virgaviridae family includes the genus *Furovirus, Hordevirus, Pecluvirus, Pomovirus, Tobamovirus*, and *Tobravirus*. In some embodiments, the rod-shaped plant virus belongs to the genus *Tobamovirus*. In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are about 300 nm in length and about 18 nm in diameter. Negatively stained electron microphotographs show a distinct inner channel of about 4 nm.

The plant virus or virus-like particles can be obtained according to various methods known to those skilled in the art. In some embodiments where plant virus particles are used, the virus particles can be obtained from the extract of a plant infected by the plant virus. For example, cowpea mosaic virus can be grown in black eyed pea plants, which can be infected within 10 days of sowing seeds. Plants can be infected by, for example, coating the leaves with a liquid containing the virus, and then rubbing the leaves, preferably in the presence of an abrasive powder which wounds the leaf surface to allow penetration of the leaf and infection of the plant. Within a week or two after infection, leaves can be harvested and viral nanoparticles extracted. In the case of cowpea mosaic virus, 100 mg of virus can be obtained from as few as 50 plants. Procedures for obtaining plant picornavirus particles using extraction of an infected plant are known to those skilled in the art. See Wellink J., Meth Mol Biol, 8, 205-209 (1998). Procedures are also available for obtaining virus-like particles. Saunders et al., Virology, 393(2):329-37 (2009). The disclosures of both of these references are incorporated herein by reference.

The nanoparticles electrostatically coupled to the plant virus or virus-like particles can include at least one of plant virus or virus-like particles, dendrimers, metallic particles, inorganic particles, polymer particles, or liposomes that have a different surface charge than the plant virus or virus-like particles. For example, the plant virus or virus-like particle can have a negative or anionic surface charge and the nanoparticle electrostatically coupled to the plant virus or virus-like particle can have an overall positive or cationic surface charge.

In some embodiments, the nanoparticles can have a maximum length or diameter of about 100 nm. In general, the nanoparticles can have dimensions small enough to allow the nanoparticles to be electrostatically coupled to the plant virus or virus-like particles.

The nanoparticles may be uniform (e.g., being about the same size) or of variable size. Particles may be any shape (e.g., spherical or rod shaped), but are preferably made of regularly shaped material (e.g., rod shaped). Other geometries can include substantially spherical, circular, triangle, quasi-triangle, square, rectangular, hexagonal, oval, elliptical, rectangular with semi-circles or triangles and the like. Selection of suitable materials and geometries are known in the art.

In some embodiments, the nanoparticles electrostatically coupled to the plant virus or virus-like particles can include charged polymers, such as positively charged dendrimers. In one embodiment, the dendrimer is a polyamidoamine dendrimer. Dendrimers or dendrons can be synthesized from monofunctional cores. One skilled in the art will recognize that other dendrimer compositions, such as polylysine, poly (propylenimine), peptide and DNA based dendrimers, and degradable cationic dendrimers, may also be employed. Examples of dendrimer compositions and synthetic methods may be found in U.S. Pat. Nos. 6,113,946, 4,631,337, 4,558,120, 4,871,779, 4,857,599, and 5,648,186, Sadler, et al., "Peptide dendrimers: applications and synthesis," Reviews in Molecular Biotechnology, 90:195-229 (2002), Stiriba, et al., "Dendritic Polymers in Biomedical Applications: From Potential to Clinical Use in Diagnostics and Therapy," Angewante Chemie International Edition, 41:1329-1334 (2002), and Funhoff, et al., "Polymer Side-Chain Degradation as a Tool to Control the Destabilization of Polyplexes," Pharmaceutical Research, 21:170-176 (2004), the contents of all of which are incorporated herein by reference. One skilled in the art will recognize how to adapt the methods of these publications to make dendrons by using monofunctional cores.

The dendrimer size is determined by the number of synthetic generations. For each generation, the volume of the dendrimer increases faster that its surface area, so that the ultimate possible size of the dendrimer is determined by steric hindrance at the free ends where the next generation of monomer is added. The desired size of the dendrimer depends on the desired buffering capacity and the desired reaction time, since each generation must be added sequentially. The dendrimers may be prepared with between 3 and 10 generations, for example, 4-6 generations.

In some embodiments, the nanoparticle construct can be in the form of a micro-aggregate that includes a plurality of the electrostatically coupled dendrimers and the plant virus or virus-like particles. Micro-aggregates of the electrostatically coupled dendrimers and the plant virus or virus-like particles can be readily injected in a subject to be treated. Micro-aggregates can also have diameters large enough to prevent passive diffusion of the micro-aggregates across blood vessels following intraperitoneal injection into a subject; thus requiring disassembly or lymphatic drainage for eventual clearance from the subject. For example, micro-aggregates of the electrostatically coupled dendrimers and the plant virus or virus-like particles can have an average hydrodynamic radius of about 100 nm to about two microns.

In some embodiments, micro-aggregates of the electrostatically coupled dendrimers and the plant virus or virus-like particles can be assembled in aqueous solutions with salt concentrations up to about 100 nM. Upon administration to a subject the micro-aggregates can gradually disassemble in a sustained manner at physiological salt concentrations over a defined period the time, such as about 1 day, 2 days, 3 days, 4 days, 5 days, 6 days, 1 week, 2 weeks or more.

In other embodiments, the nanoparticle construct can have a three-dimensional periodic nanoscale architecture, such as hierarchical complex with defined alternating electrostatically coupled layers of the plant virus or virus-like particles and the nanoparticles. The nanoparticles used to form the electrostatically coupled layers can include plant virus or virus-like particles that have differing surface charges. For example, tobacco mosaic virus (TMV) can be genetically engineered to display a corona of lysine residues on its solvent exposed surface that alters the surface charge of the TMV sufficiently to allow layer by layer electrostatic coupling of the TMV to TMV-lys.

Figure 8:
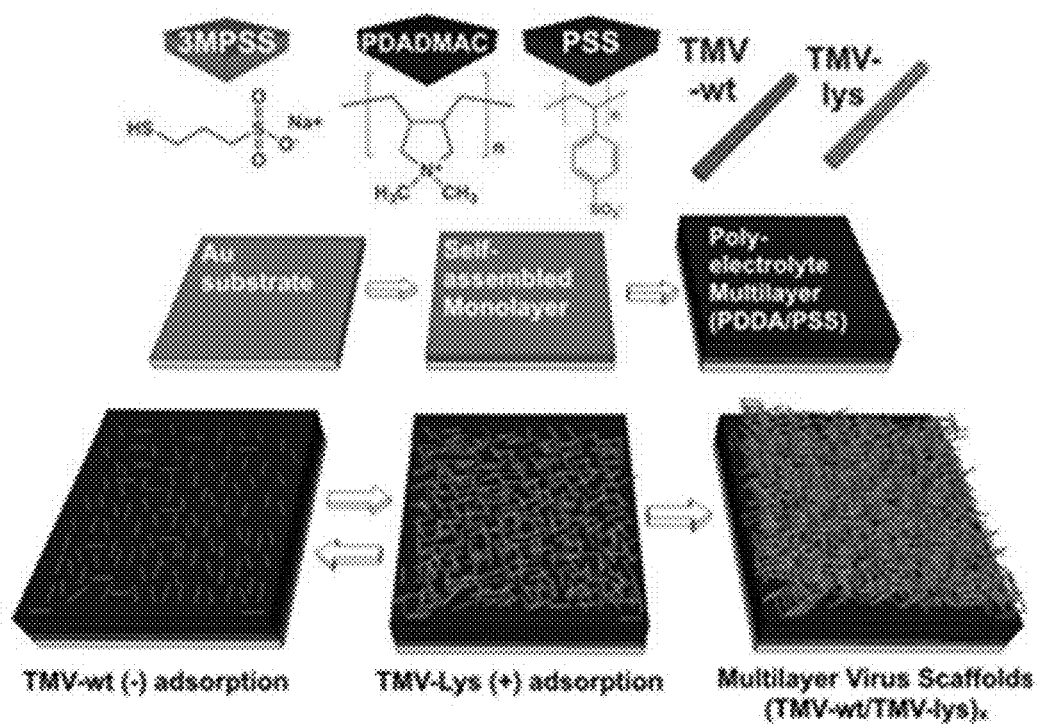
FIG. 8 illustrates a schematic illustration of the sequential formation of multilayer virus scaffolds via layer by layer (LbL) deposition of tobacco mosaic virus (TMV-wt) nanoparticles and mutant TMV particles with lysine residues (TMV-lys).

By way of example, FIG. 8 illustrates formation of the electrostatic layer by layer (LBL) assembly of TMV nanoparticle-based assemblies. First, a strong covalent Au-thiol linkages can be utilized in modifying a gold-coated glass substrate or quartz crystal with a sulfonate-terminated self-assembled monolayer (SAM), which results to a negatively charged surface. Then, in order to ensure the formation of uniform charges on the surface, an electrostatic polyelectrolyte multilayer coating can be applied by alternately immersing the thiol-modified Au-coated substrate in aqueous solutions of strong polyelectrolytes PDADMAC (1 mg/mL) and PSS (2 mg/mL). The layer-by-layer deposition of oppositely charged polyelectrolytes can be repeated for 1.5 more times leaving the polycation PDADMAC as the terminating layer, which is capable of inducing the adsorption of anionic TMV-wt nanoparticles through electrostatic interactions. The resulting polyelectrolyte LbL deposition, which is denoted as (PDADMAC/PSS)2.5 can be employed as the solid support for assembling TMV-wt and TMV-lys.

In some embodiments, the nanoparticle constructs can be loaded with one or more cargo molecules and/or bioactive agents. In some embodiments, the cargo molecule and/or bioactive agent can be loaded by covalently attaching the cargo molecule and/or bioactive agent to a reactive molecule on a surface (interior or exterior) of one or more plant virus or virus-like particles and/or nanoparticles of the nanoparticle construct. In other embodiments, the nanoparticle construct can be loaded with cargo molecules and/or bioactive agents that associate with and/or are electrostatically coupled to the plant virus or virus-like particles and/or nanoparticles of the nanoparticle construct. In some embodiments, the nanoparticle construct can be loaded with a plurality, or a substantial number of cargo molecules and/or bioactive agents. For example, in some embodiments, from about 50 to about 500 cargo molecules are loaded per nanoparticle construct, while in other embodiments from about 50 to about 200 cargo molecules are loaded per nanoparticle construct.

A variety of different types of cargo molecules and/or bioactive agents can be loaded into or onto the nanoparticle constructs. Cargo molecules and/or bioactive agents are generally relatively small organic or inorganic molecules. In some embodiments, the cargo molecules have a molecular weight ranging from about 50 to about 5000 daltons, with some embodiments being directed to cargo molecules having a weight ranging from about 50 to about 1000 daltons, or from about 100 to about 500 daltons. Examples of cargo molecules are imaging agents and therapeutic agents such as antitumor agents.

In some embodiments, the nanoparticle construct is modified to carry an imaging agent. Examples of imaging agents include fluorescent compounds, radioactive isotopes, and MRI contrast agents. For example, in some embodiments, the imaging agent is a fluorescent molecule for fluorescent imaging. The imaging agent can be any material having a detectable physical or chemical property. Such imaging agents have been well-developed in the field of fluorescent imaging, magnetic resonance imaging, positive emission tomography, or immunoassays and, in general, most any imaging agent useful in such methods can be applied to the present invention. Thus, an imaging agent is any composition detectable by spectroscopic, photochemical, biochemical, immunochemical, electrical, optical or chemical means. Means of detecting imaging agents are well known to those of skill in the art. Thus, for example, where the imaging agent is a radioactive compound, means for detection include a scintillation counter or photographic film as in autoradiography. Where the imaging agent includes a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label.

Examples of imaging agents that can be used include magnetic beads (e.g., Dynabeads), fluorescent dyes (e.g., fluorescein isothiocyanate, AlexaFluor555, Texas red, rhodamine, and the like), radiolabels (e.g., $^{3}$H, $^{14}$C, $^{35}$S, $^{125}$I, $^{121}$I, $^{112}$In, 99mTc), other imaging agents such as microbubbles (for ultrasound imaging), $^{18}$F, $^{11}$C, $^{15}$O, (for Positron emission tomography), $^{99}$mTC, $^{111}$In (for single photon emission tomography), and chelated lanthanides such as terbium, gadolinium (e.g., chelated gadolinium), and europium or iron (for magnetic resonance imaging). The choice of imaging agent depending on sensitivity required, ease of conjugation with the compound, stability requirements, available instrumentation, and disposal provisions.

In some embodiments, the imaging agent is a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Lanthanide elements are known to be useful as contrast agents. The lanthanide chemical elements comprises the fifteen metallic chemical elements with atomic numbers 57 through 71, and include lanthanum, cerium, praseodymium, neodymium, promethium, samarium, europium, gadolinium, terbium, dysprosium, holmium, erbium, thulium, ytterbium, and lutetium. Preferred lanthanides include europium, gadolinium, and terbium. In order to more readily handle these rare earth metals, the lanthanides are preferably chelated. In some embodiments, the lanthanide selected for use as a contrast agent is gadolinium, or more specifically gadolinium (III). Gadolinium contrast agents are generally chelated to facilitate attachment to the virus particle. Examples of effective gadolinium chelating molecules include 1,4,7,10-tetraazacyclododecane-1,4,7,10-tetraacetic acid (DOTA), diethylenetriaminopentacetate (DTPA), 1,4,7,10-tetraazacyclododecane-1,4,7-triasacetic acid (DO3A), 6-amino-6-methylperhydro-1,4-diazepinetetraacetic acid (AAZTA), and 4-carboxyamido-3,2-hydroxypyridinone (HOPA).

In other embodiments, the cargo molecule and/or bioactive agent can be a therapeutic agent. Examples of therapeutic agents include cardiovascular drugs (e.g., antihypertensive drugs, antiarrhythmic agents, and diuretics), neuropharmaceuticals (e.g., analgesics, anesthetics, and antipsychotics), gastrointestinal drugs (e.g., anti-ulcer drugs, antiemetics, and gastroprokinetic agents), respiratory tract agents (e.g., anthasthamtic or antiallergic drugs), antiinfective agents (antibiotics, antimycotics, and antiviral agents), endocrine-affecting drugs (e.g., steroids, hormones, and contraceptives), anti-inflammatory drugs, immunosuppressant drugs, and antitumor agents.

In some embodiments, the therapeutic agents used as cargo molecules are small molecule antitumor agents. One advantage of using antitumor agents as cargo molecules is the ability of virus particles to preferentially associate with tumor cells. Examples of small molecule antitumor agents include angiogenesis inhibitors such as angiostatin K1-3, DL-α-difluoromethyl-ornithine, endostatin, fumagillin, genistein, minocycline, staurosporine, and thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine .beta.-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, deguelin, 5,6-dichlorobenz-imidazole 1-beta-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives thereof.

The cargo molecules and/or bioactive agents can be conjugated to the nanoparticle constructs by any suitable technique, with appropriate consideration of the need for pharmacokinetic stability and reduced overall toxicity to the patient. The term "conjugating" when made in reference to an agent and a nanoparticle construct as used herein means covalently linking the agent to plant virus or virus-like particles and/or nanoparticles of the nanoparticle construct subject to the limitation that the nature and size of the agent and the site at which it is covalently linked to the plant virus or virus-like particles and/or nanoparticles of the nanoparticle construct do not interfere with the biodistribution of the plant virus or virus-like particles and/or nanoparticles of the nanoparticle construct. The cargo molecule can be linked to the interior or the exterior of plant virus or virus-like particles and/or nanoparticles of the nanoparticle construct, while in some embodiments the cargo molecule is linked to both the interior and the exterior of the plant virus or virus-like particles and/or nanoparticles of the nanoparticle construct. In some embodiments, where the cargo molecule is linked to a plant virus or virus-like particle, the location of the cargo molecule on the interior or exterior is governed by the amino acids of viral coat proteins that are selected as reactive sites.

Cargo molecules and/or bioactive agents can be coupled to a nanoparticle construct either directly or indirectly (e.g., via a binder group). In some embodiments, the molecule and/or agent is directly attached to a functional group capable of reacting with the agent and/or molecule. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). Further, viral coat proteins contain tyrosines, which can be modified using diazonium coupling reactions. In addition, genetic modification can be applied to introduce any desired functional residue, including non-natural amino acids, e.g., alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

In other embodiments, a chemical binder group can be used. A binder group can serve to increase the chemical reactivity of a substituent on either the agent or the plant virus or virus-like particles and/or nanoparticles of the nanoparticle construct, and thus increase the coupling efficiency. Binder chemistries can include maleimidyl binders, which can be used to bind to thiol groups, isothiocyanate and succinimidyl (e.g., N-hydroxysuccinimidyl (NHS)) binders, which can bind to free amine groups, diazonium which can be used to bind to phenol, and amines, which can be used to bind with free acids such as carboxylate groups using carbodiimide activation. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a binder group. Coupling can be effected, for example, through amino groups, carboxyl groups, sulfhydryl groups or oxidized carbohydrate residues.

Other types of binding chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide binder wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, the surface of the nanoparticle construct can be modified by attachment of something other than a cargo molecule. For example, the virus particle multimer can be modified to include PEGylation, cell penetrating peptides, or targeting molecules. The nanoparticle construct can be modified either before loading with cargo molecules, or after loading with cargo molecules. Targeting molecules can be attached to the outside of the nanoparticle construct in order to guide the nanoparticle constructs to a particular target tissue, such as tumor tissues. Examples of targeting molecules include peptide ligands (e.g., RGD, bombesin, or GE11), vitamins such as folic acid, and other tumor-homing proteins such as transferrin, as well as and antibodies such as Herceptin or any other antibody or antibody fragment with tumor-specific properties, and DNA-, RNA-, or PNA-based aptamers that specifically bind to an antigen present on the target tissue, such as a tumor antigen. Cell penetrating peptides can also be attached to the outside of the nanoparticle constructs to encourage internalization of the nanoparticle constructs. Cell penetrating peptides are generally relatively short, amphipathic peptides. Examples of cell penetrating peptides include TAT sequence or polyArginine peptides.

In some embodiments, rather than covalent attachment, cargo molecules and/or bioactive agents can also be loaded into or onto the nanoparticle constructs in a non-covalent manner by associating them with nucleic acid present within the plant virus particles of the nanoparticle construct. While not intending to be bound by theory, it appears that the cargo molecule associates with the nucleic acid as a result of the affinity of the cargo molecule and/or bioactive agent for the nucleic acid. Affinity is the tendency of a compound to naturally associate with another object (e.g., a nucleic acid). Affinity is influenced by non-covalent intermolecular interactions between the compound and the object, such as hydrogen bonding, electrostatic interactions, hydrophobic interactions, and Van der Waals forces.

An example of cargo molecules having an affinity for the nucleic acid are cargo molecules having a positive charge. One skilled in the art can readily determine whether a cargo molecule has affinity for the nucleic acid within a plant virus particle. For example gel mobility shift assays, oligonucleotide crosslinking assays, optical absorbance and fluorescence assays, calorimetric assays, and/or surface Plasmon resonance assays to determine the association and dissociation kinetics and affinities of cargo molecules for nucleic acids.

Furthermore, any drug or imaging agent exhibiting low affinity can be readily modified with a small, positively charged tag or complementary oligonucleotide to bind to nucleic acid within a plant virus particle. For some embodiments, the cargo molecules interact with nucleic acids in a reversible manner, in order to facilitate release of the cargo molecules in or to the target tissue.

In some embodiments, a targeting molecule can also be attached to the nanoparticle constructs. By "targeting molecule" herein is meant a molecule which serves to target or direct the nanoparticle construct and/or plant virus or virus-like particles and/or nanoparticles released from the nanoparticle construct to a particular location, cell type, diseased tissue, or association. In general, the targeting molecule is directed against a antigenic site. Thus, for example, antibodies, cell surface receptor ligands and hormones, lipids, sugars and dextrans, alcohols, bile acids, fatty acids, amino acids, peptides and nucleic acids may all be attached to localize or target the plant virus or virus-like particles, nanoparticles, and/or nanoparticle construct to a particular site. In some embodiments, the targeting molecule allows targeting of the plant virus or virus-like particles, nanoparticles, and/or nanoparticle construct to a particular tissue or the surface of a cell.

In some embodiments, the targeting molecule is a peptide. For example, chemotactic peptides have been used to image tissue injury and inflammation, particularly by bacterial infection; see WO 97/14443, hereby expressly incorporated by reference in its entirety. Another example, are peptides specific to fibrin or vascular cell adhesion molecules to direct the imaging probe to sites of inflammation, such as an atherosclerotic plaque. In other embodiments, the targeting molecule is an antibody. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin.

In some embodiments, the antibody is directed against a cell-surface marker on a cancer cell; that is, the antigenic site is a cell surface molecule. As is known in the art, there are a wide variety of antibodies and antibody fragments known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In some embodiments, the targeting molecule is all or a portion (e.g., a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. Receptor ligands include ligands that bind to receptors such as cell surface receptors, which include hormones, lipids, proteins, glycoproteins, signal transducers, growth factors, cytokines, and others.

In some embodiments, the nanoparticle construct can be directed to a target tissue in a subject by in situ delivery and/or administration to the tissues. In particular, plant virus or virus-like particles have been shown to preferentially accumulate in diseased tissue, such as cancer tissue or inflamed tissue (e.g., atherosclerotic blood vessels). While not intending to be bound by theory, it appears that plant virus particles are taken up by blood components such as macrophage cells of the immune system, which subsequently accumulate in diseased tissue (e.g., a tumor or atherosclerotic blood vessel), thereby delivering the virus particle to cells at the disease site.

In some embodiments, administering the nanoparticle construct to a subject can generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Other embodiments described herein relate to methods of treating cancer in a subject in need thereof by administering in situ to cancer of the subject a therapeutically effective amount of the nanoparticle construct, which includes a plurality of plant virus or virus-like particles and a plurality of nanoparticles having a different surface charge than the plant virus or virus-like particles electrostatically coupled to the plant virus or virus-like particles. While not intending to be bound by theory, it appears that the plant virus particles or virus-like particles have an anticancer effect as a result of eliciting an immune response to the cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the nanoparticle constructs are used to treat cancer selected from the group consisting of but not limited to melanoma, breast cancer, colon cancer, lung cancer, and ovarian cancer. In some embodiments, the virus particles are used to treat lung cancer.

In some embodiments, the in situ administration of the nanoparticle construct can be proximal to a tumor in the subject or directly to the tumor site to provide a high local concentration and sustained and/or controlled release of the plan virus or virus-like particle in the tumor microenvironment. The method represents a type of in situ vaccination, in which application of an immunostimulatory reagent directly to the tumor modifies the tumor microenvironment so that the immune system is able to respond to the tumor.

In some embodiments, the method can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

In some embodiments, the step ablating the cancer includes administering a therapeutically effective amount of an anticancer agent to the subject. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin, rapamycin, thapsigargin, and bikunin, and derivatives (as defined for imaging agents) thereof.

In some embodiments, the step ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers).

In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches.

In passive specific cancer immunotherapy substances with specificity for certain structures related to cancer that are derived from components of the immune system are administered to the patient. The most prominent and successful approaches are treatments with humanised or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations.

On the other hand, active specific cancer immunotherapy aims at antigen-specific stimulation of the patient's immune system to recognize and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches relies on manipulating dendritic cells (DC) as the most important antigen presenting cell of the immune system. For example, loading with tumor antigens or tumor cell lysates, transfection with genes encoding for tumor antigens and in-vivo targeting are suitable immunotherapies that can be used together with the virus or virus-like particles of the invention for cancer treatment.

When used in vivo, the nanoparticle constructs can be administered as a pharmaceutical composition, comprising a mixture, and a pharmaceutically acceptable carrier.

The nanoparticle constructs, or pharmaceutical compositions comprising these particles, may be administered by any method designed to provide the desired effect. Administration may occur enterally or parenterally; for example orally, rectally, intracisternally, intravaginally, intraperitoneally or locally. Parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The formulations may be conveniently presented in unit dosage form and may be prepared by any of the methods well known in the art of pharmacy. Preferably, such methods include the step of bringing the virus particles into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect.

One skilled in the art can readily determine an effective amount of the nanoparticle constructs to be administered to a given subject, by taking into account factors such as the size and weight of the subject; the extent of disease penetration; the age, health and sex of the subject; the route of administration; and whether the administration is local or systemic. Those skilled in the art may derive appropriate dosages and schedules of administration to suit the specific circumstances and needs of the subject. For example, suitable doses of the virus particles to be administered can be estimated from the volume of cancer cells to be killed or volume of tumor to which the virus particles are being administered.

Useful dosages of the nanoparticle constructs can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the nanoparticle constructs can vary depending upon many different factors, including means of administration, target site, physiological state of the patient, whether the patient is human or an animal, other medications administered, and whether treatment is prophylactic or therapeutic.

Advantageously, the nanoparticle construct can provide a slow-release and/sustained formulation of the plant virus or virus-like particles as an in situ vaccine that maintains sustained immune stimulation without the need for repeat injections. The release of the plant virus or virus-like particles can be constant and sustained for about 1 day, 2 days, 3 days, 4 days, 5 days, 6 days, 1 week, 2 weeks or more. The constant release can be sustained between subsequent nanoparticle administrations. Maintaining a constant immunostimulatory effect can reduce the number of administrations, enhancing their effectiveness. The release can be defined by strength of the electrostatic interaction between the particles and the pH and/or physiological salt concentration of the tissue to which the nanoparticle construct is administered.

Examples have been included to more clearly describe particular embodiments of the invention. However, there are a wide variety of other embodiments within the scope of the present invention, which should not be limited to the particular examples provided herein.

EXAMPLES

Example 1

Slow-Release Formulation of Cowpea Mosaic Virus In Situ Vaccine for Treatment of Ovarian Cancer We have demonstrated the efficacy of the plant virus cowpea mosaic virus (CPMV) as an immunotherapy for a variety of cancer types, including ovarian cancer. CPMV, administered into the intraperitoneal space, acts as an in situ vaccine priming a systemic anti-tumor immune response. An in situ vaccine works through direct administration into the local tumor environment to reverse tumor-mediated immunosuppression and resensitize the immune system to tumor specific antigens. By induction of a more general immune response, in situ vaccines are not limited by the presence of known antigens in tumor tissue. We previously demonstrated that in a syngeneic, orthotopic mouse model of ovarian cancer, weekly intraperitoneal (IP) treatment using the CPMV in situ vaccine significantly improved survival.

To alleviate the need for repeat administration, we set out to develop a slow-release formulation of the CPMV in situ vaccine that would maintain sustained immune stimulation without the need for IP repeat injections. Maintaining a constant immunostimulatory effect could reduce the number of IP administrations, making this treatment more translatable. While IP infusions of chemotherapies are currently approved for use clinically, and have been shown to provide a survival advantage in the treatment of ovarian cancer, this method of administration is underutilized, likely due to the cost and inconvenience when compared to intravenous (IV) administration of chemotherapy. In contrast to IV administration that can be done in the out-patient setting, IP administration often requires a hospital admission leading to increased cost and decreased quality of life.

A number of slow-release formulations of cancer drugs and immunotherapies are currently under investigation; these include hydrogels for delayed release of tumor associated antigens, chemotherapeutics, and a variety of other cargo including nucleic acids as well as and microneedle administration of antibodies for immunotherapy. These diverse approaches all seek to improve cancer treatment by maintaining a constant therapeutic concentration and reducing the number of administrations.

In this work, we aimed to develop slow-release assemblies of CPMV making use of charged dendrimers and electrostatic self-assembly protocols. While zwitterionic in nature, CPMV carries an overall negative surface charge, therefore we chose to program co-assembly with positively-charged polyamidoamine (PAMAM) dendrimers. Virus-dendrimer assemblies have previously been explored as a method to create well-controlled higher order structure on a nanoscale-to-mesoscale level, however their potential for biomedical applications has not yet been fully explored. Here I explore the assembly and disassembly of a CPMV dendrimer hybrid, as well as its IP trafficking and efficacy in a mouse model of ovarian cancer.

Materials and Methods

Preparation of CPMV Nanoparticles and Generation 4 PAMAM Dendrimer

Cowpea mosaic virus (CPMV) was propagated in black-eyed pea plants (*Vigna unguiculata*) and isolated using previously reported protocols.

For biodistribution studies, the CPMV particles were conjugated with an Alexa Fluor® 647 dye (NHS-AF647) using a previously described reaction. In brief, dye labeling was carried out overnight at a concentration of 2 mg/mL CPMV in 0.1 M potassium phosphate buffer (pH 7.0) and 10% DMSO with an excess of 2,000 dyes per CPMV. The dye-functionalized CPMV particles (CPMV-AF647) were purified by ultracentrifugation and characterized using UV-visible absorption spectroscopy and SDS-PAGE.

Generation 4 polyamidoamine (PAMAM) dendrimers with an ethylenediamine core (10 wt. % in methanol) used in the study was purchased from Sigma Aldrich. PAMAM-G4 or G4 was isolated by removing methanol through rotary evaporation and resuspended in MilliQ water at a 10 mg/mL concentration.

Dynamic Light Scattering (DLS)

To study the assembly and disassembly of CPMV-G4 dynamic light scattering (DLS) measurements were performed: CPMV (~50 mg/mL in 0.1 M PBS, pH 7.0) and PAMAM-G4 dendrimers (10 mg/mL in MilliQ water) were mixed at 0.15 mg/mL of virus and 0.15 mg/mL dendrimer concentration. The ionic strength was modified by adding small amounts of either 2 M NaCl or 10×PBS stock solutions. The hydrodynamic radius of the virus-polymer assemblies was measured using a DynaPro Nanostar DLS instrument (Wyatt Technology, Goleta, CA) at a wavelength of 658 nm, 90° scattering angle, 25° C.

Atomic Force Microscopy

The morphology of the CPMV-G4 assemblies was imaged using a 5500 atomic force microscope (Keysight Technologies, Inc., formerly Agilent Technologies) in tapping mode. High-resolution noncontact gold-coated NSG30 silicon cantilevers (NT-MDT Spectrum Instruments, Tempe, AZ) with a resonant frequency of 240-440 kHz were used and mounted onto the piezoelectric scanner for AFM imaging. The resulting AFM images were processed using Gwyddion Ver. 2.47.

Ovarian Cancer In Vivo Efficacy and Biodistribution

Animal studies were carried out using IACUC-approved protocols. Female C57BL/6 mice (Jackson Labs) were injected intraperitoneally with 2 million cells of the highly aggressive, luciferase-positive, murine ovarian cancer cell line ID8-Defb29/Vegf-A in sterile PBS. ID8-Defb29/Vegf-A cells were a generous gift from Dr. Fiering (Dartmouth College) and luciferase was stably transfected in this cell line as previously described. Cancer cell growth was monitored using the Perkin Elmer IVIS Spectrum In vivo imaging system; mice were injected intraperitoneally with luciferin (15 mg/mL, 150 µL intraperitoneally) and imaged five minutes post-injection with a three-minute exposure time. Total luminescence was determined using Living Image® software and total counts per mouse were graphed. Treatment was initiated seven days following cell injection and administered either weekly (PBS and CPMV 100 µg per mouse), once (1 mg CPMV in the described CPMV-G4 assembly), or every three weeks (1 mg CPMV). CPMV-G4 was vortexed immediately prior to injection. Prior to treatment group assignment, total luminescence was determined on day seven and used to match total cancer burden between treatment groups (n=5). Mice were humanely euthanized when total body weight was greater than 20% more than body weight predicted by established growth curves, indicating a high volume of ascites.

For biodistribution studies, mice were injected with 2 million ID8-Defb29/Vegf-Luc cells intraperitoneally and cancer cells were allowed to grow for three weeks. Following establishment of intraperitoneal disease as determined by IVIS imaging, mice were injected with PBS, 1 mg of AF647-CPMV, or 1 mg of AF647-CPMV-G4. Mice were imaged prior to injection, immediately after injection, and at times 30 min, 1 h, 6 h, 12 h, 24 h, 48 h, 72 h, 96 h, 7 days, 10 days, and 14 days. Images were obtained in Spectral unmixing mode and each time-point was unmixed to isolate AF647 signal using the same established library. ROI analysis was performed on unmixed images from each time-point and radiant efficiency ((p/sec/cm2)/(µW/cm2)).

Results and Discussion

Formation of the CPMV-G4 Assembly

The electrostatically driven assembly of the CPMV nanoparticles with the amine-decorated generation 4 PAMAM dendrimer was investigated through dynamic light scattering (DLS) measurements. Combining both components at 0.15 mg/mL concentration in pure MilliQ water immediately resulted to an increase in hydrodynamic radius from 15 nm (for wild-type CPMV) to approximately 70 nm. Increasing the ionic concentration to 10 mM NaCl abruptly induced the formation of larger aggregates with diameters greater than 1.5 µm. These large aggregates were observed at salt concentrations up to 100 mM; higher concentrations gradually disassembled the CPMV-G4 aggregates, with concentrations greater than 200 mM forming aggregates with an average of 300 nm in hydrodynamic radius (FIG. 1A). A similar trend was observed when a related experiment was conducted with increasing phosphate buffered saline (PBS) concentration. Without electrolytes, the CPMV-G4 assembly measured at 70 nm RH, which then rapidly increased to about 2 microns from 0.07 to 0.36×PBS. At PBS concentrations higher than 0.36×, the hydrodynamic radius averaged 300 nm (FIG. 1B). These data indicate that the presence of a low salt concentration promotes formation of larger aggregates; while CPMV and the G4 dendrimers still have some interaction at 0 salt concentration, as indicated by the measured hydrodynamic radius of 70 nm, the repulsion between the positively charged G4 limits greater aggregation in the absence of ions for some electrostatic shielding. When the salt level is increased too high however, salt screening effects limit the interactions between the dendrimers and virus, thus reducing overall aggregate size. These properties are thought be useful for in vivo biomedical applications, i.e., the use of slow-release formulation: at low salt the assembly is triggered, and post-injection into the tissue, under physiologic salt concentrations release is induced.

The stability of the CPMV-G4 assembly was investigated by storing the mixture in a low ionic strength environment (25 mM NaCl) for a week, disassembled by gradually increasing the salt concentration, and held in high ionic strength conditions (300 mM NaCl) for another week. The assembly maintained its large hydrodynamic radius at low salt concentrations for 7 days. Exposure to higher ionic concentrations (150-300 mM NaCl) led to a burst release into smaller aggregates with an RH of 500 nm; then slow decrease in size that may indicate slow-release of CPMV from the smaller aggregates (FIG. 1C).

For animal studies, the concentration of CPMV was increased to 2.5 mg/mL in order to form larger aggregates and reduce the total volume of injection necessary; the CPMV:G4 ratio was maintained at 1:1 and salt concentration was kept low (25 mM NaCl). Due to the high concentration of CPMV and G4, large aggregates formed immediately and RH could not be determined by DLS, supporting that the aggregates were at least larger than 2.5 µm. A cloudy appearance was observed immediately and aggregates were collected at the bottom of the tube following a brief spin using a tabletop centrifuge (FIG. 1D), indicating successful formation of CPMV-dendrimer aggregates. The colloidal suspension was mixed well prior to use in animals.

The morphologies of the assemblies were further investigated through tapping mode-atomic force microscopy. A 0.15 mg/mL solution of CPMV, in the absence of the G4 dendrimer, shows areas of packed CPMV when cast on a freshly cleaved mica surface, however the presence of large empty spaces demonstrates that there are not strong interactions between the nanoparticles (FIG. 2A). In contrast, when 0.15 mg/mL CPMV is mixed with G4 at a 1:1 ratio in a salt-free solution, particles form large areas of tightly packed CPMV nanoparticles on the surface (FIG. 2B). Increasing the ionic concentration to 50 mM NaCl induced formation of stacks of packed CPMV nanoparticles (FIG. 2C), indicating further increased interactions between CPMV and the G4 dendrimers. At higher ionic concentration (150 mM NaCl) a layer of tightly arranged CPMV, similar to the formation observed in the absence of salt formed (FIGS. 2B&D), supporting that high salt concentrations reduce formation of large aggregations. Overall, the morphological variations of the CPMV-G4 assembly correlate to the DLS hydrodynamic radius measurements, which exhibit the responsive assembly and disassembly of the electrostatic interactions as a function of salt concentration.

These findings are in agreement with previous work showing that increasing salt concentrations reduce the size of aggregate formation through reducing electrostatic interactions between dendrimers and viral particles. While salt concentration has been known to be important in the assembly formation of virus-dendrimer hybrid materials, to our knowledge, the disassembly of these hybrid materials has not been investigated or utilized for biomedicine. These data indicate that while the large aggregates are stable for extended periods of time at low salt concentrations, the larger structures disassemble at ionic concentrations found in the IP space (approximately 150 mM). Even at the highest salt concentration measured however, virus-dendrimer aggregates would still be too large to passively diffuse across blood vessels to enter systemic circulation from the intraperitoneal space (size limit <100 nm) and would require disassembly or lymphatic drainage for eventual clearance. Further, the long-term stability of the aggregates at low salt concentrations makes this assembly a promising candidate for continued presence in the IP space.

Treatment of Ovarian Cancer in a Syngeneic Mouse Model

Treatment efficacy of the CPMV-G4 formulation was assessed using a syngeneic, orthotopic mouse model of ovarian cancer. Treatment was started 1 week following injection of 2 million ID8-Defb29/Vegf-A-Luc cells into the intraperitoneal space. Establishment of disease was confirmed and then monitored using IVIS imaging. Body weight was also monitored in order to track development of ascites. Groups were treated with the following treatments: 1 mg of CPMV administered twice vs. a single dose 1 mg CPMV equivalent of CPMV-G4 vs.100 μg of free CPMV administered weekly (which is the dosing previously shown to be effective at treating ovarian cancer growth); controls received 1 mg PAMAM-G4 or PBS. Disease burden was monitored twice weekly by tracking total luminescence indicating cancer cell growth (FIG. 3). Tumor development was monitored until the onset of ascites development was observed. Bioluminescence tracking was not performed following the onset of ascites as the development of ascites has been shown to reduce accuracy of bioluminescent measurements.

Tumor burden in mice treated with a single dose of CPMV-G4 closely matched total luminescence observed in mice treated more frequently with a lower dose of free CPMV for the first three weeks of treatment, delaying cancer cell growth significantly (FIG. 3). While the higher dose of free CPMV given less frequently did slow tumor growth, this difference was not statistically different from the PBS control. Further, the G4 administered without CPMV did not slow tumor growth, indicating that the improved effect of the CPMV-G4 assemblies compared to free CPMV was due to virus-dendrimer aggregates (and not presence of G4), leading to the continued presence of the immunostimulatory CPMV in the IP space. The retention of CPMV in the IP space was further tested through examining the biodistribution of fluorescently labeled CPMV administered alone or with G4.

Biodistribution of CPMV-G4 Administered Intraperitoneally

Figure 4A:
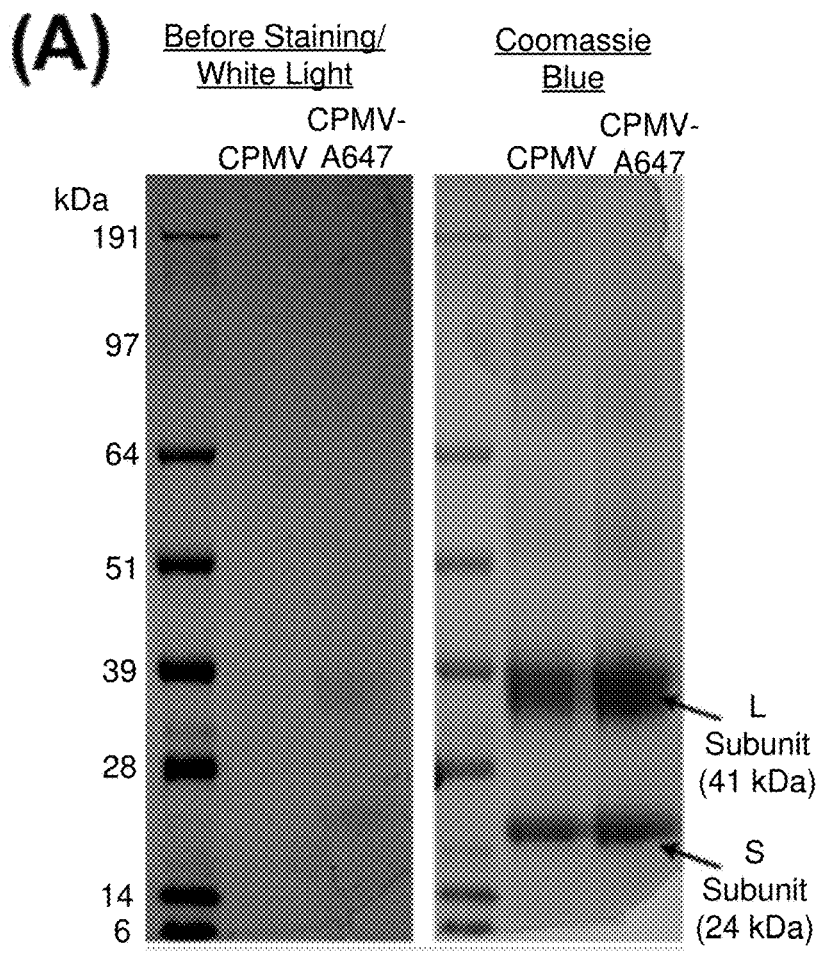
FIGS. 4(A-C) illustrate the characterization of dye-labeled CPMV and CPMV-G4 assemblies (A) UV-Vis absorption spectra of CPMV-AF647 particles. (B) SDS-PAGE analysis of wild type CPMV and CPMV-AF647 in white light and after Coomassie Blue staining. (C) Free CPMV-AF647 and aggregates of CPMV-AF647-G4 immediately following mixing and after a brief spin in a table-top centrifuge.
Figure 4B:
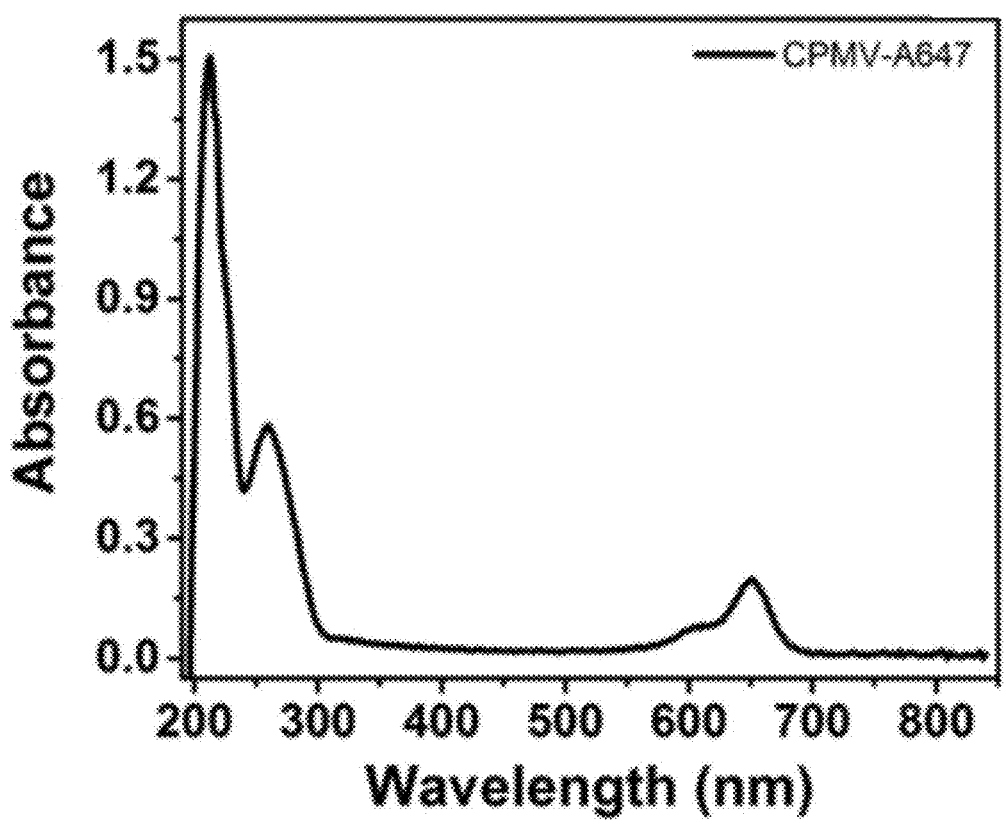
Figure 4C:
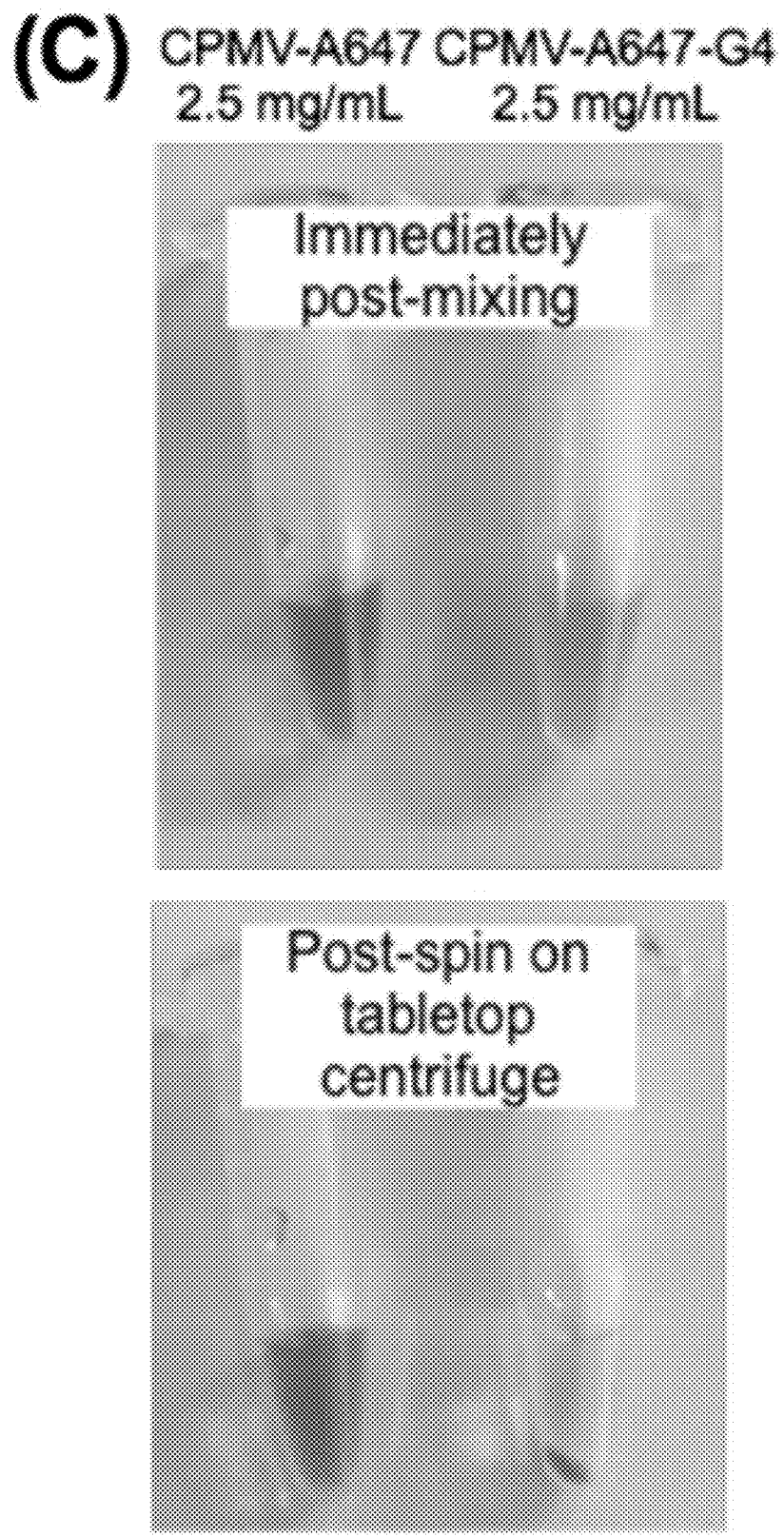

The biodistribution and clearance rate of CPMV compared to CPMV-G4 was evaluated using in vivo fluorescence imaging (Spectrum BLI). Mice were injected with 1 mg of CPMV labeled with AlexaFluor 647 either as free CPMV or formulated as the CPMV-G4 assembly as described above. CPMV nanoparticles were covalently functionalized with NHS-AF647 dye molecules using the exposed lysine residues on the capsid surface. The successful chemical labeling of the CPMV particles post purification was verified using UV-Vis absorption spectroscopy; about 50 dyes per CPMV were attached (FIG. 3A). SDS gel electrophoresis was also conducted to confirm the covalent conjugation of AF647 dye molecules to the CPMV coat proteins (FIG. 4B). Under white light, bright blue bands were observed matching the small and large subunit proteins of CPMV-AF647, which was not evident for CPMV; staining with Coomassie Blue, shows that CPMV coat proteins are colocalized with the dye. Aggregation was confirmed by immediate visual changes in the mixture as well as accumulation in the bottom of an eppendorf tube following a 30 second spin on a tabletop centrifuge.

Figure 5A:
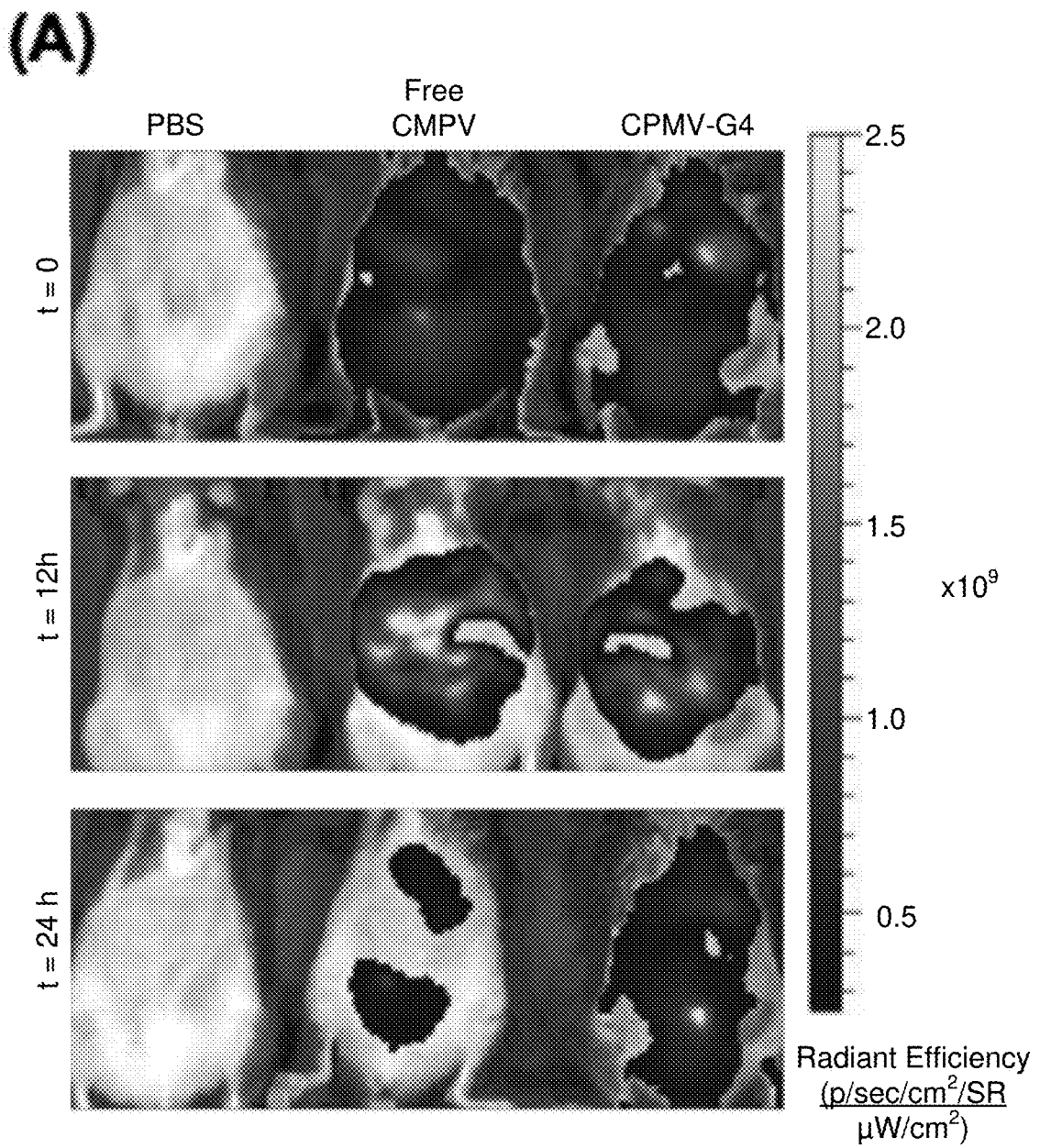
FIGS. 5(A-C) illustrate biodistribution of CPMV and CPMV-G4 in the intraperitoneal space. (A) Fluorescence imaging of C57/BL6 mice immediately following injection, at 12 and 24 hours. (B) Fluorescence imaging of C57/BL6 mice at 1 and 11 days (C) Normalized fluorescent intensity as determined by ROI analysis; the total fluorescence measured in the intraperitoneal space immediately following injection was established as 1 and relative intensity for all subsequent time-points was calculated as a portion of this intensity.
Figure 5B:
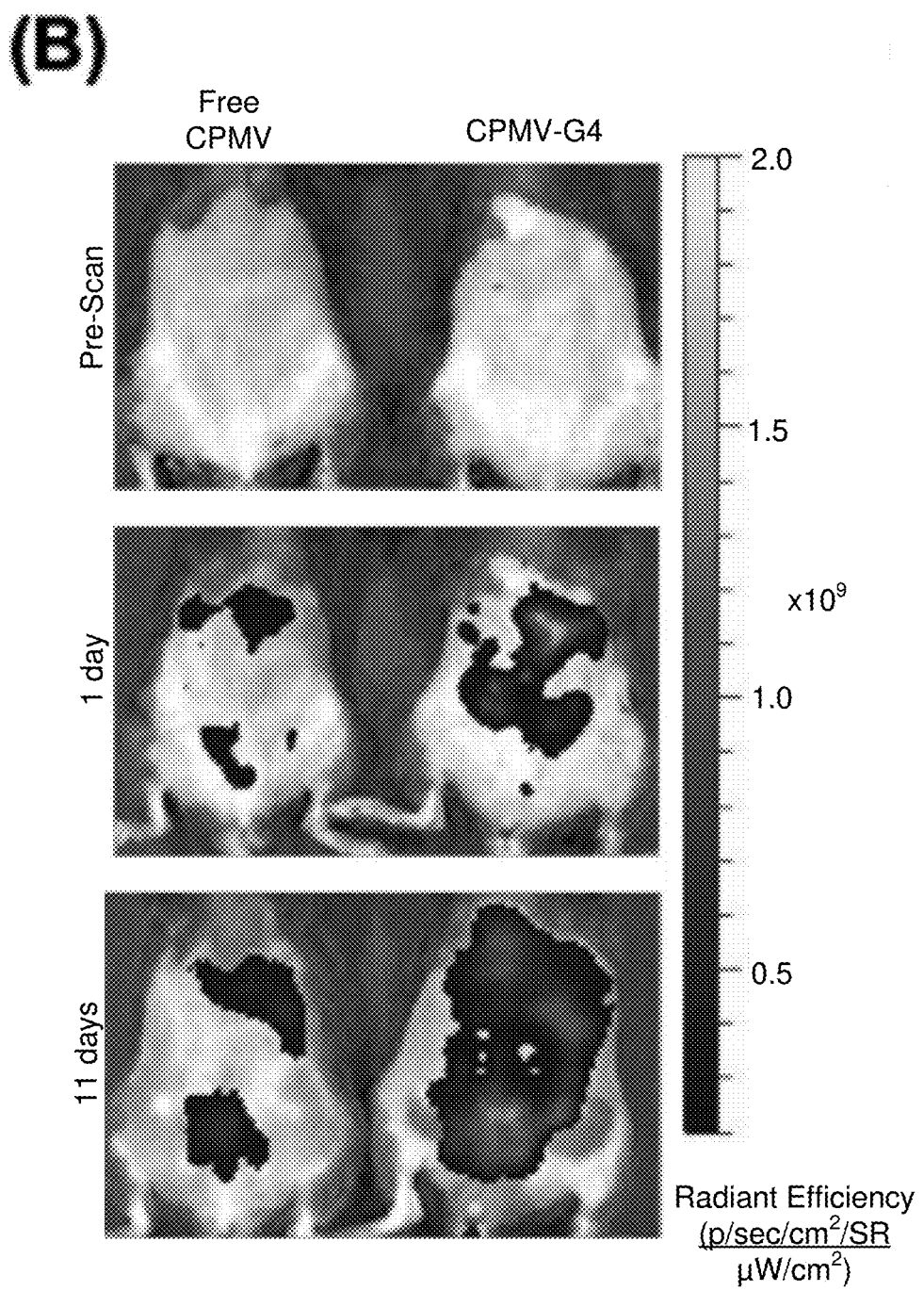
Figure 5C:
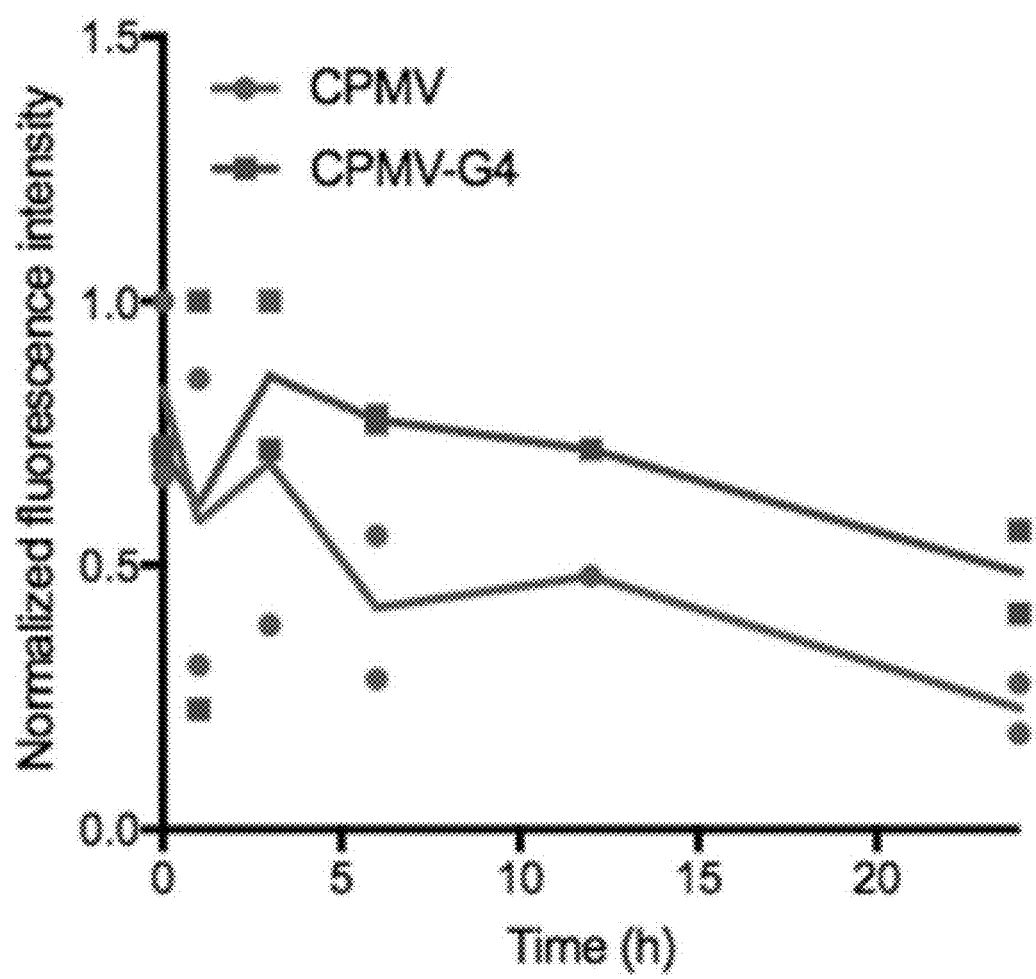

Biodistribution was then determined using a longitudinal imaging approach; at defined time points over an 11-day course total fluorescence in the IP space was determined using in vivo fluorescence imaging (Spectrum BLI) and region of interest (ROI) analysis (FIG. 5). Free CPMV was cleared relatively quickly from the IP space, only approximately 25% of the initial fluorescence was still present at 24 hours post-injection; in contrast, 50% of initial fluorescence was present in the CPMV-G4 assembly treated mice. Further, in a very preliminary study (n=1), CPMV-G4 was still present in the intraperitoneal space at day 11 (FIG. 5B). The initial increase in fluorescence observed in some early time-points might be due to a reduction in fluorescence quenching of the fluorophores; perhaps as the CPMV spread throughout the IP space, the overall concentration of fluorophores was reduced and measured fluorescence increased. In order to prevent this early quenching from causing artificially high percent retention to be calculated, relative fluorescence intensity was calculated from the maximum fluorescence measured and not the initial intensity measurement. Current studies are ongoing to repeat this biodistribution with lower fluorophore conjugation in an attempt to reduce this quenching effect. While this quenching effect limits the utility of in vivo fluorescent imaging to determine the absolute concentration of CPMV still present in the IP space, it still provides useful information as to the relative speed at which free CPMV and CPMV-G4 assembly is cleared.

While work is still ongoing to repeat this experiment and further time-points need to be measured, these biodistribution studies are in good agreement with the efficacy studies supporting that CPMV in the CPMV-G4 assemblies is present for a longer amount of time, continually stimulating antitumor immunity. As the larger CPMV-G4 aggregates cannot be cleared through leaking into blood vessels in the IP space, they must either first dissemble or be cleared from through the lymphatic system. This retention is longer than other polymer-based hydrogels injected intraperitoneally which were found to persist at 8 days following injection. Additionally, while hyaluronic acid based hydrogels have been shown to persist in the IP space for a comparable or longer time, their use as a drug carrier has led to both decreased and increased tumor growth, indicating that further investigation of this system, especially its degradation byproducts, is needed before it can be considered for use in slow-release formulations. Finally, this system has several advantages over other types of slow-release formulations including implantable devices that typically require an invasive surgery; the virus-dendrimer colloidal solution is non-viscous and can be administered with a syringe without surgical intervention.

Virus-dendrimer hybrid materials are novel class of materials with the potential for a number of potential applications. Here we present one such potential use of these hybrids for delayed release of the immunostimulatory nanoparticle CPMV. By inducing the formation of aggregates in the intraperitoneal space, this CPMV-G4 hybrid is able to increase the retention of CPMV allowing for continued immune stimulatory and an enhanced antitumor response compared to the same dose of "free" CPMV. While still preliminary, this represents an important potential application of virus-dendrimer aggregates to improve treatment efficacy and quality of life by reducing the number of necessary administrations while maintaining a potent immunotherapy effect.

Example 2

The complex and functional nanostructures ubiquitous in living organisms are dynamic roadmaps in constructing novel nanomachines for material science and providing solutions in biomedical research. One of the most elegant and efficient nanofabrication techniques in living systems is based on molecular self-assembly wherein chemically and structurally compatible biological components spontaneously form hierarchical arrangements driven by non-covalent interactions. Nanotechnology is taking advantage of the same principle through the bottom-up fabrication of highly ordered surfaces, interfaces and architectures for sensing, catalysis, delivery, coatings, plasmonics, and electronic devices. Under this area, common nanoscale building blocks or molecular tools include metallic nanoparticles, protein cages, colloidal latex particles, self-assembling peptides, dendrimers, and carbon-based nanomaterials.

The tobacco mosaic virus (TMV-wt) is a well-known rigid, rod-shaped VNP with dimensions of 300 nm×18 nm with a 4 nm central channel and a positive-sense single stranded RNA genome. The TMV-wt capsid is comprised of 2,130 identical coat proteins that self-assembled into a helical structure around its genomic material. The overall surface charges of TMV-wt can be tuned with respect to its isoelectric point (pI) of ~3.5. Hence, in pH>pI, TMV-wt can be considered as an anionic macromolecule. Genetic engineering allows to alter the surface charges; and in this work we consider TMV-wt and TMV-lys, the latter is a genetic variant with a Threonine-to-Lysine substitution at amino acid position 158. TMV-lys displays a corona of lysine side chains on its solvent exposed surface (FIG. 6). The successful LbL assembly of TMV-wt with multilayers of polyethyleneimine and polyacrylic acid has been previously demonstrated. However, after immobilizing a layer of TMV-wt on the surface, at least 12 bilayers of polyelectrolytes are required in order to deposit another set of TMV-wt, thus limiting this approach. Aside from electrostatics, multilayer arrays of VNPs, including other particles such as cowpea mosaic virus (CPMV) and cowpea chlorotic mottle virus (CCMV), have also been achieved using biotin-streptavidin interactions but the size and the tetrameric cubic structure of streptavidin (4-6 nm) might hinder direct contact between the binding mediators.

To overcome these technological hurdles, we formed a hierarchical assembly using TMV-wt and TMV-lys. We demonstrate a robust and scalable LbL process allowing the 3-dimensional TMV scaffolds to be released into freely-standing biomembranes.

Since the topological features of TMV-wt are within the nanoscale ranges of the 3D-fibrous network of the extracellular matrix (ECM), such 3D self-assembled networks of TMV may find applications in regenerative medicine. In fact, recent reports have demonstrated that 2D substrates coated with TMV-wt can support the differentiation of bone marrow stromal cells (BMSCs) into osteoblasts. The functionalization of the TMV-wt scaffold with various cell binding ligands has been demonstrated to program cell adhesion to the TMV featured surfaces. In another report, the surface of TMV-wt was coated with polyaniline doped with poly(styrenesulfonate), which supported the growth of PC12 neuronal cells. With potential applications in regenerative medicine in mind, we explored the capability of the multilayer virus assemblies to support the adhesion of NIH-3T3 fibroblast cells for tissue engineering applications. Furthermore, the TMV-programmed films and membranes can be used in drug delivery and vaccine technology. Toward this goal, we demonstrate the self-assembly of free-standing biomembranes using cargo-functionalized TMV building blocks.

Materials

The following chemicals were purchased from Sigma Aldrich (St. Louis, MO): poly(diallyldimethylammonium chloride) solution (MW: 200,000-350,000), poly(sodium 4-styrene-sulfonate) (MW: ~70,000), sodium 3-mercapto-1-propane sulfonate, cellulose acetate, propargyl amine, HEPES buffer solution, N-(3-dimethylaminopropyl)-N'-ethylcarbodiimide (EDC), hydroxybenzotriazole, aminoguanidine hydrochloride, ascorbic acid, copper sulphate, potassium phosphate salts, glutaraldehyde, and Fluoroshield™ with DAPI histology mounting medium. The Alexa Fluor 488 azide, DMEM (Dulbecco's Modified Eagle Medium) media (with 10% Fetal Bovine Serum (FBS)), sulfuric acid, and hydrogen peroxide (30% purity) were purchased from Thermo Fisher Scientific (Waltham, MA). Standard AT-cut 5 MHz gold-coated QCM crystals (1 in diameter, 25° C.) were used for quartz crystal microbalance studies.

Propagation of TMV-wt and TMV-lys

Both the wild-type TMV and mutant TMV-lys virus particles were cultivated by mechanical inoculation in *Nicotiana benthamiana* (Tobacco) plants using 5-10 μg of viruses per leaf. The virions were then extracted and purified using previously reported standard procedures. Successful isolation and structural integrity of the particles were determined using fast protein liquid chromatography (FPLC), sodium dodecyl sulphate polyacrylamide gel electrophoresis (SDS-PAGE), and transmission electron microscopy (TEM), and atomic force microscopy (AFM).

To conjugate fluorescent dye molecules onto the TMV-wt, (denoted as TMV-i488), the particle was first functionalized with interior alkynes (TMV-iAlk) using EDC coupling in 0.1 M HEPES buffer, pH 7.4 over 24 hours using 15 equivalents of propargylamine per coat protein, 30 equivalents of EDC (10 equivalents at a time added at 0, 6, and 18 hours), and 30 equivalents of hydroxybenzotriazole. After purification by ultracentrifugation pelleting over a sucrose cushion at 42,000 rpm for 2.5 hours, Alexa Fluor 488 azide was attached by click chemistry: TMV-iAlk was incubated on ice for 30 mM with 5000 molar excess of dye in the presence of 2 mM aminoguanidine, 2 mM L-ascorbic acid, and 1 mM copper sulfate in 10 mM potassium phosphate buffer, pH 7.0. TMV-i488 was then purified by ultracentrifugation as outlined above.

Quartz Crystal Microbalance (QCM) Apparatus

The real-time adsorption of virus nanoparticles on a flat solid substrate was monitored using a QCM200 quartz crystal microbalance from Stanford Research Systems (Sunnyvale, CA) in a flow injection analysis (FIA) setup, as schematically illustrated in FIG. 7A. The main substrate used for the adsorption measurements was a commercially available 5 MHz, AT-cut, 1-in diameter quartz crystal coated with gold that was mounted on the accompanying crystal holder and sealed with an axial flow cell adapter. A maximum of 150 μL of fluid comes into contact with the surface of the QCM crystal. The flow cell was connected to a 50-mL glass syringe that contains the buffer through a 6-port injection valve (IDEX Health & Science, Oak Harbor, WA). Aside from the buffer and the QCM flow cell, the valve was also attached to a 250 μL-sample port wherein the adsorbing particle can be loaded and injected onto the QCM flow cell without any disturbance in the frequency and motional resistance signals as monitored by the built-in software of the QCM instrument. The injection valve can be manually set to "load" and "inject" positions; each position alters the fluid flow within the ports. For a typical adsorption measurement, the valve was initially set to "load" and the buffer was allowed to enter port #1 (refer to FIG. 7B), which was directly connected to port #2 and to the QCM chamber. While the QCM signal was stabilizing and still in the "load" position, the sample was injected through port #5, which was connected to port #3, to sample loop, port #4, and then port #6. Once a stable QCM signal was achieved, the valve was switched to the "inject" position wherein the buffer flows from port #1, then through the sample loop (where the sample was stored), and to port #2 and the QCM flow cell.

Fabrication of the Multilayered Viral Assemblies

Prior to any QCM measurement, the quartz crystal was first immersed in a Piranha solution, which is composed of 70% sulfuric acid and 30% hydrogen peroxide (30% purity), for 1-3 minutes to remove any organic contaminants. The crystal is then rinsed with copious amounts of water, dried with nitrogen, and exposed to oxygen plasma treatment (30

W) for 1 min. Afterwards, a negatively charged self-assembled monolayer was tethered onto the gold surface by immersing the QCM crystal in an aqueous solution containing 20 mM sodium 3-mercapto-1-propane-sulfonate (3MPSS) from Aldrich for at least 10 hr. To functionalize the surface with uniform charges, a polyelectrolyte-based layer-by-layer film was formed on the Au QCM crystal. Using a Carl Zeiss HMS series programmableslide stainer, the thiol-modified QCM crystals were alternately immersed in aqueous solution containing 1 mg/mL poly(diallyldimethyl ammonium chloride) (PDADMAC, MW=200,000-350,000, Sigma-Aldrich) and another solution with 2 mg/mL poly (styrenesulfonic acid) (PSS, MW=70,000, Sigma-Aldrich) for 20 min each. After every immersion in either the polycation or polyanion solution, the substrate is rinsed in MilliQ water for 5 mM. The layer-by-layer deposition of the polyelectrolyte multilayers was repeated until 2.5 bilayers of PDADMAC and PSS was achieved thus resulting to a positively charged surface. The polyelectrolyte LbL film will be referred to as (PDADMAC/PSS)x, wherein x is the number of bilayers.

The polyelectrolyte-modified Au QCM crystal was then mounted onto the QCM flow cell assembly. A potassium phosphate buffer (pH 5.0, 10 mM) was loaded onto the 50-mL glass syringe in the FIA setup and was set to run at 30 µL/min. The QCM200 instrument was then initialized to record the changes in frequency and motional resistance as a function of time. After the signals reached a stable baseline, 250 µL of 0.1 mg/mL TMV-wt in the same buffer was injected through the sample port. The QCM measurement was allowed to continue until the frequency has finished decreasing and the signal has stabilized. After drying the QCM crystal, the flow cell assembly was setup again and a 250 µL solution of 0.1 mg/mL TMV-lys in the same potassium phosphate buffer (pH 5.0, 10 mM) was injected and allowed to adsorb. The process was continued until multiple layers have been immobilized on the surface. The LbL-type multilayer virus assemblies are denoted as (TMV-wt/TMV-lys)x, wherein x is the number of bilayers composed of TMV-wt and TMV-lys that have been adsorbed.

Preparation and Release of the Free-Standing Biofilms of TMV-wt-TMV-lys

Plain microscope BK7 glass slides were cut into 2.5 cm×1.5 cm pieces and rinsed in Fisher sonicating solution for 15 mM, Milli-Q water (18.2 MΩ cm resistivity) for 5 min, acetone for 5 mM and Milli-Q water again for another 5 mM. Then, the substrates were further immersed in piranha solution for 30 mM. After rinsing with large amounts of water, the glass slides were then sonicated in Milli-Q water and acetone for 10 min each and exposed to oxygen plasma treatment for 3 min.

Before any polyelectrolyte or virus nanoparticle deposition, a sacrificial cellulose acetate (CA) layer was initially deposited on the pre-cleaned glass substrates instead of modifying the surface using a thiol-based self-assembled monolayer. A 7 wt % CA solution in acetone was spin-casted onto glass at 1000 rpm for 30 sec. This step was repeated for multiple times until a sufficiently thick layer was formed. Afterwards, the negatively-charged CA-modified glass substrate was immersed in a 10 mM PDADMAC solution (with 1 M NaCl) for 30 min. The substrates were then alternately submerged in a polyanionic solution composed of 10 mM PSS and 1 M NaCl and in the polycationic solution with 10 mM PDADMAC and 1 M NaCl for 1 min each. In between immersions, the substrate was rinsed in MilliQ water for 1 min. The polyelectrolyte layer-by-layer deposition was repeated until 50 bilayers were achieved. The virus nanoparticles were then introduced by alternately spin-casting TMV-wt and TMV-lys solutions with 0.1 mg/mL concentration in potassium phosphate buffer (pH 5, 10 mM) at 1000 rpm for 1 min. The polyelectrolyte/virus nanoparticle films were submerged in acetone, which dissolved the CA sacrificial layer and released the freely standing virus film.

Cell culture and Optical Microscopy Imaging

The gold substrates coated with virus nanoparticle assemblies were placed into 6 well tissue culture plates, and each well were seeded with $8\times10^5$ cells and incubated at 37° C. for 24 hour. Afterwards, the cells were washed three times with phosphate buffer saline (PBS) solution (pH 7.4). Next, the cells were fixed using 3% (v/v) glutaraldehyde for 10 minutes, and then rinsed once more with PBS. The cells were then permeabilized with 1 ml of 0.2% (w/v) Triton X-100 PBS solution for 5 min and washed again for 3 times with PBS. Fixed cells were incubated with Actin green 488 (2 drops/mL of PBS, ThermoFisher Scientific) for 3 minutes and washed 3 times with PBS. 5 µL/mL DAPI (SouthernBiotech, Birmingham, AL) in PBS was used to stain the cell nuclei for 10 minutes and cells were washed 3 times with PBS. Film samples were mounted on glass slides with nail polish and images were taken via a laser scanning confocal microscope (Leica TCS SP5 Confocal) from Leica Microsystems, Inc. (Buffalo Grove, IL).

Characterization of TMV-wt and TMV-lys and their Multilayer Assemblies

The zeta potential measurements were performed using the Zetamaster particle electrophoresis analyser setup (Malvern Instruments Ltd., Malvern, UK) with a 5 mW HeNe laser ($\lambda$=633 nm) based from a potential range of −120 to 120 mV and 10 measurements per particle.

The virus nanoparticles including TMV-wt, TMV-lys, and TMV-i488 were characterized using sodium dodecyl sulfate-polyacrylamide gel electrophoresis (SDS-PAGE). 20 µg of particles were denatured into coat proteins by exposure to 100° C. for 5 min and were run onto an SDS gel at 200 V for 1 hr in 1×MOPS running buffer. The gels were then exposed to UV light to ensure successful fluorescent labeling of TMV-i488, eventually stained using Coomassie blue, and visualized using an AlphaImager imaging system (Biosciences).

Transmission electron microscopy (TEM) was used to image the VNPs. The particles were diluted to a concentration of 0.1 mg/mL in PBS (pH 7.4), adsorbed onto Formvar-carbon-coated copper grids (Electron Microscopy Sciences, Hatfield, PA), and negatively stained with 2% (w/v) uranyl acetate for 2 minutes. The samples were then imaged using a Zeiss Libra 200FE TEM at 200 kV.

The VNPs and the step-by-step formation of the LbL viral assemblies were imaged using tapping-mode atomic force microscopy (AFM). The AFM measurements were performed using a PicoScan 2500 AFM (Agilent Technologies), which is equipped with a piezo scanner set to scan the films at 1-1.5 lines/sec. Tapping mode cantilevers (NSG30, single crystal silicon, NT-MDT) with a resonant frequency in the range of 240-440 kHz were used for imaging. The Gwyddion Software (Ver. 2.19) was used to filter and analyze all AFM images.

The free-standing virus assemblies were imaged using a Maestro fluorescence imaging system using the green filter set (503 to 548 nm excitation filter, 560 nm longpass emission filter). The surface morphology of the released-films was characterized using scanning electron microscopy (SEM). The free-standing films were laid onto clean glass slides and sputtered with 5 nm of gold using a Hummer 6.2 Sputter system from Anatech USA (Alexandria, VA). A JEOL scanning electron microscope (JEOL-JSM-6510LV) was then used for SEM imaging wherein the working distance and acceleration voltage were set to 14-15 mm and 30 kV respectively.

Results and Discussion

QCM Adsorption Studies of the LbL Deposition of TMV-wt and TMV-lys

The step-by-step formation of the electrostatic LbL assembly of TMV nanoparticle-based assemblies is illustrated in FIG. 8. First, the strong covalent Au-thiol linkages were utilized in modifying a gold-coated glass substrate or quartz crystal with a sulfonate-terminated self-assembled monolayer (SAM), which results to a negatively charged surface. Then, in order to ensure the formation of uniform charges on the surface, an electrostatic polyelectrolyte multilayer coating was applied by alternately immersing the thiol-modified Au-coated substrate in aqueous solutions of strong polyelectrolytes PDADMAC (1 mg/mL) and PSS (2 mg/mL). The layer-by-layer deposition of oppositely charged polyelectrolytes was repeated for 1.5 more times leaving the polycation PDADMAC as the terminating layer, which is capable of inducing the adsorption of anionic TMV-wt nanoparticles through electrostatic interactions. The resulting polyelectrolyte LbL deposition, which is denoted as (PDADMAC/PSS)2.5 was employed as the solid support for assembling TMV-wt and TMV-lys.

Based on the literature, the isoelectric point (pI) of TMV-wt lies at pH~3.5; hence, at pH values higher than this pI, the rod-shaped virus nanoparticle is considered to be an anionic macromolecule. On the other hand, the lysine residues incorporated on the genetically engineered TMV-lys causes a more positive overall surface charge for the particle. Zeta potential measurements were performed to confirm the net surface charge of the particles in potassium phosphate buffer solution. Taking the pI of TMV-wt into account, the pH of the experiments was fixed at 5. The potentials were determined to be −18.3±0.8 mV and −8.0±1.5 mV respectively for TMV-wt and TMV-lys respectively. While reversion of surface charge from negative to positive could not be achieved through the single point mutation (Thr→Lys), we hypothesized that the corona of Lys side chains on the TMV surface would provide a strong driving force in the electrostatic assembly of these particles.

To verify whether these complimentary TMV particles are electrostatically compatible to form LbL assemblies, quartz crystal microbalance (QCM) measurements were performed in flow injection mode. The QCM is a powerful analytical tool in monitoring adsorption, desorption or structural rearrangements of various materials that occur on the surface of a circular AT-cut quartz crystal probe. Both sides of the quartz crystal are coated with metallic electrodes. Due to the piezoelectric property of the quartz crystal, internal mechanical stresses on the crystal can be induced whenever an external potential is applied between its electrodes. If an oscillating electric potential is applied across the QCM probe, a pure shear vibration at a characteristic resonant frequency Fo propagates across the crystal. This oscillation and thus the resonant frequency are highly sensitive to any changes in mass as a result of any adsorption or desorption phenomena. In general, decreasing frequency shifts correlate to an increased mass measured or adsorption. The inverse relationship between changes in the resonant frequency $\Delta f$ and mass changes $\Delta m$ is quantified by the Sauerbrey equation (Eq. 1):

$$\Delta f = \left(-2F_0^2/(A\sqrt{\rho\mu})\right) \times \Delta m \quad (1)$$

where A (cm) is the sensor surface area, $\rho$ (2.648 g/cm) is the density of quartz and $\mu$ ($2.947\times10^{11}$ g/(cm s$^2$)) is the shear modulus of quartz. Considering these constants, the Sauerbrey equation can then be simplified to Eq. 2:

$$\Delta m = -C_f \times \Delta f \quad (2)$$

where $C_f$ corresponds to the sensitivity factor, equal to 22.438 ng/(cm$^2$ Hz) specific to quartz crystals with an exposed electrode area of 1.27 cm$^2$.

Figure 9A:
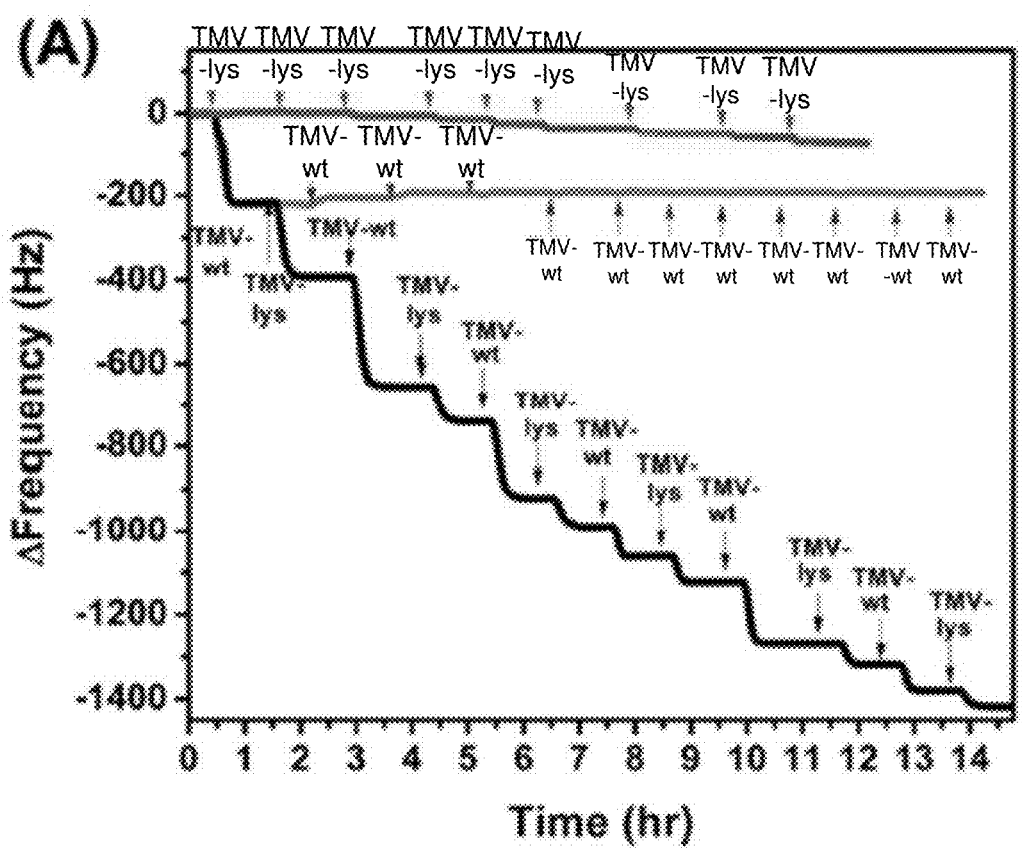
FIGS. 9(A-D) illustrate QCM Studies of the LbL assembly of TMV-wt and TMV-lys: (A) QCM $\Delta f$ plots of alternating depositions of TMV-wt and TMV-lys and repeated depositions of a TMV-wt-only and a TMV-lys-only system (control) (B) Surface coverage of each depositiion of TMV-based particles during the LbL process (C) Overlaid $\Delta f$ and $\Delta R$ plots of the LbL assembly (D) $\Delta R$ and $\Delta f$ plots showing the behavior of a purely elastic (1) and viscous system (2) with the LbL adsorption of TMV-wt and TMV-ly.

FIG. 9A presents the time-dependent adsorption of alternating injections of TMV-wt and TMV-lys in contrast to control systems, which consist of repeated injections of a single-type of virus nanoparticles (either TMV-wt only or TMV-lys only). In both alternating TMV-wt/TMV-lys and the TMV-wt only systems, injecting the first layer of TMV-wt resulted to a significant adsorption on the PDADMAC-terminated Au-coated QCM crystal. The $\Delta f$ corresponding to the first injection of TMV-wt was measured to be 215.4 Hz, which corresponds to 4.83 µg/cm$^2$ according to the Sauerbrey equation (FIG. 9B). Comparing this value against the theoretical adsorption values of closely-packed TMV system leads to an estimate of the surface coverage F and manner of the TMV deposition on the polyelectrolyte-modified surface. TMV-wt is a rod-shaped particle with dimensions of 300 nm×18 nm and a molecular weight of 3.94×10$^7$ Da. A single particle, therefore, has a weight of 6.54×10$^{-17}$ g. Taking the geometrical features of the virus particle, a total of 2.35×10$^{10}$ particles, which should weigh about 1.54 µg, is required if the TMV-wt adsorbed as a monolayer in a close-packed arrangement. Since total electrode area of the QCM crystal used is 1.27 cm$^2$, the total mass adsorbed for the first injection of TMV-wt is 6.13 µg, which is 4× higher than the theoretical values. This observation may suggest that multilayers of viruses deposited instead of a monolayer; further, the theoretical adsorption value did not consider the hydration or incorporation of water molecules within these protein particles, which should translate to a larger resonant frequency shift. As illustrated in FIG. 9C, the simultaneous measurement of the shifts of motional resistance ($\Delta R$), which amounted to 78.6Ω after the first TMV layer, supports this claim since it correlates to the "dampening effect" or the dissipated energy during oscillation caused by the adsorption of viscoelastic films. An additional frequency shift is measured separate from the actual mass of the adsorbing molecule or particle whenever viscous, hydrated or swollen systems come in contact with the QCM. According to Kanazawa and Gordon, this $\Delta f$ is dependent on the square root of the viscosity and the density of the solution.

Figure 9D:
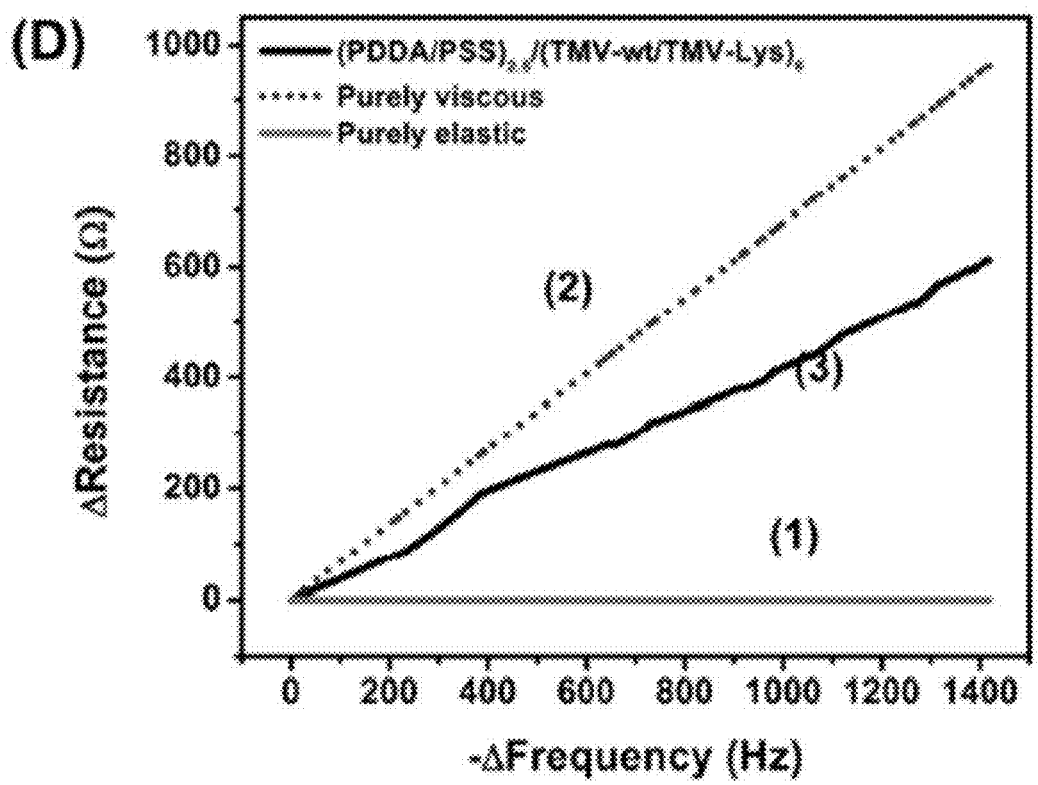

After the initial injection of TMV-wt, a solution containing TMV-lys particles was introduced into the system, which resulted to a mass uptake of 3.94 µg/cm$^2$ (175.8 Hz). As presented in FIG. 9A, the resonant frequency shifts demonstrated a significant stepwise decrease corresponding to a well-ordered LbL build up of virus particles. Adsorption of the virus-based nanoparticles typically lasts for at least 20-25 minutes to stabilize. It is important to note that the buffer was set to continuously flow at 30 µL/min all throughout the experiment and no injections were performed until 40 minutes after the Δf plateaus to verify the stability of the deposition of each virus type. For the LbL experiment of TMV-wt and TMV-lys, negligible changes were observed to occur during this window right before the next injection. The first few depositions of TMV-wt resulted to a surface coverage of 4-6 g/cm². The mass build-up per injection started to decrease after 1-2 bilayers. The same trend was observed for TMV-Lys, whose adsorption started at 3.94 μg/cm², decreased to 1.6-1.9 μg/cm², and reached 0.8-1 μg/cm². This overall trend can be attributed to the steady build-up and eventual saturation of negative charges on the surface as contributed by the overall negative charges of both TMV-based particles. Furthermore, in addition to observing the continuously increasing resistance shifts, the overall viscoelastic nature of the virus assembly can be characterized by plotting the ΔR as a function of −ΔF. For a purely elastic system, ΔR equals 0, which results to a horizontal line wherein the slope ΔR/ΔF=0 (FIG. 9D, line 1). For a purely viscous system, the resulting plot will be a line with a particularly high slope. The plot of a viscoelastic system should have a slope that lies between the purely elastic and purely viscous systems. As a point of comparison, line 2 in FIG. 2D presents the ΔR-ΔF plot for sucrose solutions with concentrations ranging from 0-25 wt %, as measured by Dixit, et al using a similar QCM flow cell setup. The slope for this sample system is 0.6788 Ω/Hz. Based from line 3 in FIG. 9D, until the first depositions of TMV-wt and TMV-lys at ΔF=384.5 Hz, the slope of the ΔR/ΔF was measured to be 0.424 n/Hz. For succeeding depositions, a slight change in the slope to 0.413 Ω/Hz was observed, which suggests that the increasing the number of deposited virus layers might have improved the rigidity of the resulting assembly.

Meanwhile, this behavior of the TMV-wt and TMV-lys system demonstrated a sharp contrast as compared to the control system wherein repeated injections of TMV-wt after the first layer did not amount to any mass build-up. In fact, after the first injection of TMV-wt, succeeding injections resulted to 0.42 μg (2$^{nd}$ injection), 0.22 μg (3$^{rd}$ injection), 43.4 ng (4$^{th}$ injection), and 17.3 ng (5$^{th}$ injection) of detached TMV-wt, which can be attributed to interparticle interactions between TMV particles. After the 5$^{th}$ injection, no further significant losses were observed with the control system. The repeated adsorption of TMV-lys was also investigated using a PSS-terminated Au QCM surfaces. Only minimal adsorption was observed: 0.13-0.28 μg of TMV-lys were gradually adsorbing on the substrate after each injection, which can be attributed to the patchy arrangement of carboxylic acid and amine units in the lysine-modified TMV mutant. This gradual deposition, however, was significantly less than the build-up demonstrated by the electrostatic assembly of TMV-wt and TMV-lys. The injection of the polycation was detected by the QCM flow setup and was adsorbed by the TMV-wt-terminated interface; however, the allotted contact time in the continuously flowing system was not sufficient to produce a stable deposition. Then, 250 μL of TMV-wt (0.1 mg/mL) was introduced, which did not attach on the surface even with another injection of wild-type TMV. This result agrees with a previous report wherein no binding of TMV-wt was achieved until 12 bilayers of polyelectrolytes were deposited after the initial TMV-wt layer. This experiment was repeated. These experiments highlight the ease in building mesoscale virus assemblies by utilizing alternately charged particles instead of using polyelectrolyte systems.

Figure 10A:
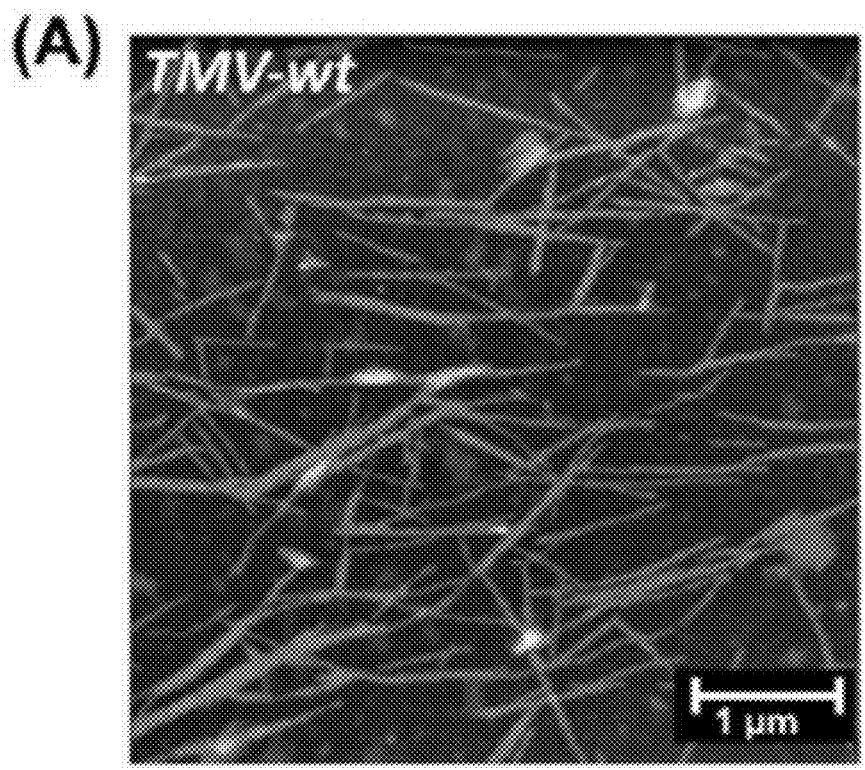
FIGS. 10(A-D) illustrate topographical tapping-mode atomic force microscopy (AFM) images of (A) TMV-wt and (B) TMV-lys. (C) and (D) are their corresponding transmission electron microscopy (TEM) images.

Atomic Force Microscopy (AFM) Studies of the LbL Deposition of TMV-wt and TMV-lys The structural integrity of the molecularly farmed plant VNPs and the gradual build-up of the LbL assembly were monitored using tapping-mode atomic force microscopy (AFM). Dilute solutions of the particles were dropcasted on cleaned glass substrates and imaged after drying. The tapping mode-AFM images (5 μm×5 μm) of TMV-wt and the mutant TMV-lys are presented in FIGS. 10A and 4B. Their corresponding transmission electron microscope (TEM) images are shown in FIGS. 10C and 10D. Both sets of micrographs demonstrate the monodisperse features of both, TMV-wt and TMV-lys. It was noted that the ends of some TMV-wt particles, are connected, as reported in previous studies. The end-to-end alignment appeared to be more profound for the TMV-wt compared to the TMV-lys counterpart.

Figure 11C:
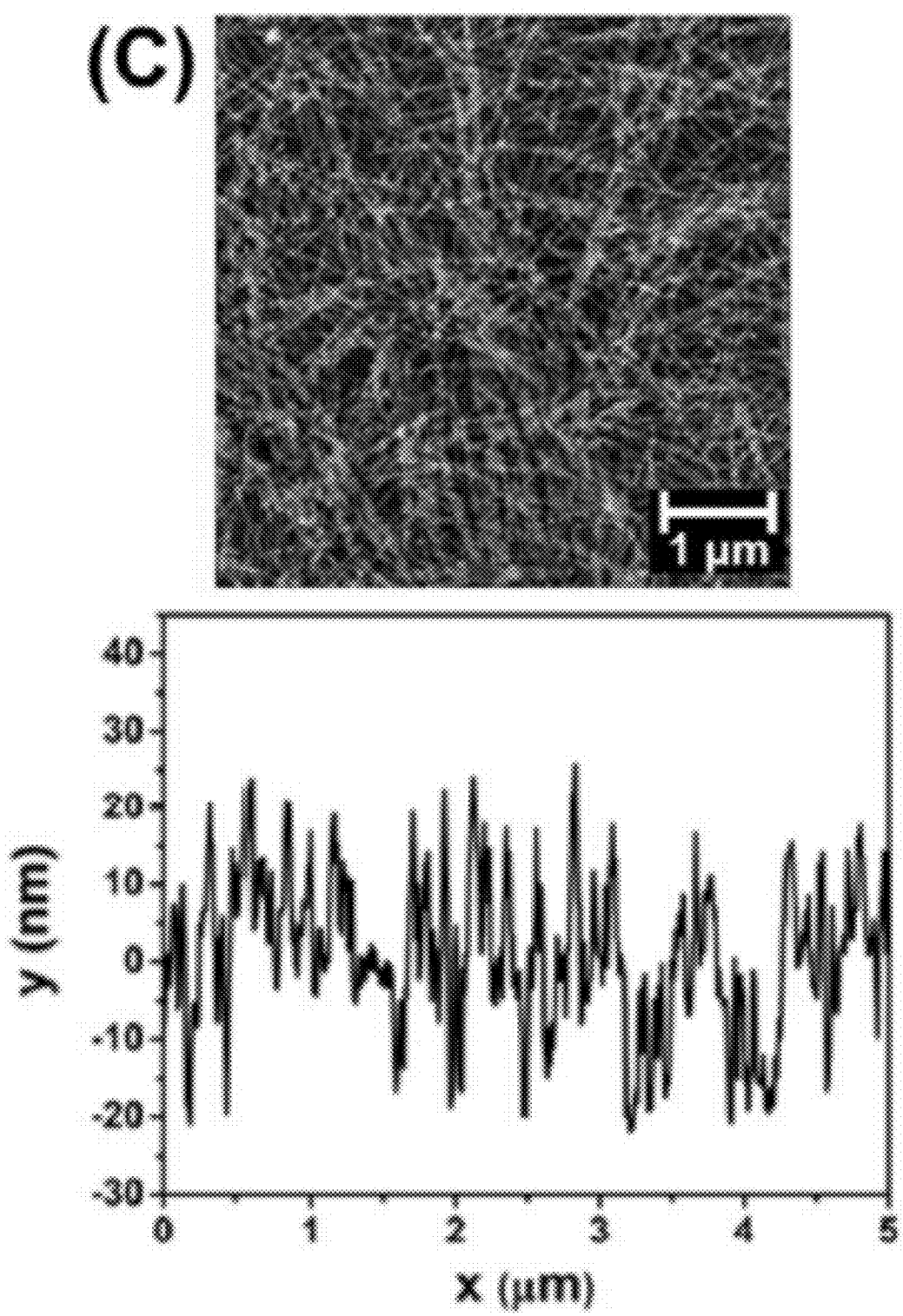
FIGS. 11(A-D) illustrate topographical tapping-mode AFM images and cross-sectionaln profiles of the (A) polyelectrolyte-modifed surface, (B) 1.5 bilayers ((TMV-wt/TMV-lys)1.5), (C) 3 bilayers ((TMV-wt/TMV-lys)3), and (D) 6 bilayers ((TMV-wt/TMV-lys)6) of TMV-wt and TMV-lys.

FIG. 11 demonstrates the series of AFM images and their cross-sectional profile following the controlled assembly of TMV-based particles via LbL deposition. As seen in FIG. 11A, the morphology of the polyelectrolyte-modified surface can be seen as a rough surface with a root-mean-square (RMS) of 4.28 nm. Determined by the Gwyddion 2.19 software, the RMS value is the root mean square average of the cross-sectional height profile of the surface. After the addition of 1.5 bilayers of TMV-wt and TMV-lys (FIG. 11B), the deposition of rod-shaped particles is evident, which increased the RMS value to nm. FIGS. 11C and 11D shows the topographical tapping-mode AFM images of 3 and 6 bilayers of TMV-wt and TMV-lys. At 3 bilayers, the RMS value reached a maximum of 11.1 nm but returned to 9.3 nm for the 6 bilayer-modified surface. Comparing the images for the 3-bilayer and 6-bilayer films, it can be observed that the TMV biofilms are more compact as the number of particle layers increase due to the electrostatic interaction. This finding is in good agreement with QCM adsorption studies in terms of the slightly increasing rigidity of the assembly of TMV.

Multilayer Virus Assemblies for Cell Adhesion Scaffolds

The topographical features of the LbL virus assemblies presented in FIG. 11 closely resemble the 3-dimensional nano-fibrous structure of the native extra-cellular matrix (ECM), which are composed of proteoglycans and various proteins such as collagen. In addition to the anisotropic characteristics of TMV, plant virus nanoparticles are also composed of repeating protein monomers that undergo self-assembly to form monodisperse hierarchical architectures. Due to these properties, the TMV is a promising candidate for tissue engineering wherein scaffolds capable of supporting and probing cellular behaviors including adhesion and differentiation are being developed. Previous reports have shown that the ordering of TMV-wt nanoparticles and the covalent attachment of cell adhesion ligand such as arginine-glycine-aspartic acid (RGD) has improved cell adhesion. Similarly, the multilayer virus assemblies have also been tested whether these surfaces can potentially be used for facilitating cell adhesion. Here, we assessed whether the programmed TMV-wt-TMV-lys arrays could serve as a platform for cell adhesion. First, quantitative studies were performed where NIH-3T3 fibroblast cells with a concentration of 2.5×10⁴ cells/mL were seeded onto the LbL virus films as well as on the blank and the polyelectrolyte-modified gold substrates. Cells were imaged and quantified using light microscopy: in reference to FIG. 6A, while only 33±4 and 49±5 cells/mm² remained on the bare gold substrate and the (PDADMAC/PSS)2.5 surfaces, 81±5, 95±10, 104±9, and 112±6 cells/mm² adhered onto 0.5, 1, 4.5, and 5 bilayers of TMV-wt-TMV-lys biofilms respectively. Next, we performed confocal imaging to also assess cell viability on the TMV featured surfaces: after 24 hr, cells were fixed, stained with ActinGreen™ 488 reagent and 4',6-diamidino-2-phenylindole (DAPI), and then imaged using fluorescence confocal microscopy (FIG. 12). ActinGreen™ is composed of the green Alexa Fluor 488 dye conjugated onto a bi-cyclic peptide phalloidin that possesses high selectivity towards F-actin filaments and enables easy visualization of the cytoskeleton. DAPI is a blue fluorescent probe staining agent for the cell nuclei. The confocal microscopy images in FIG. 12 B-E show that the surfaces supported high cell density and spreading, which suggests that the NIH-3T3 fibrolast cells are healthy. These experiments verify that the TMV-based LbL surfaces could be utilized in regenerative medicine. For example, the performance could be specifically tailored through introduction of cell growth factors or other stimuli.

Figure 13C:
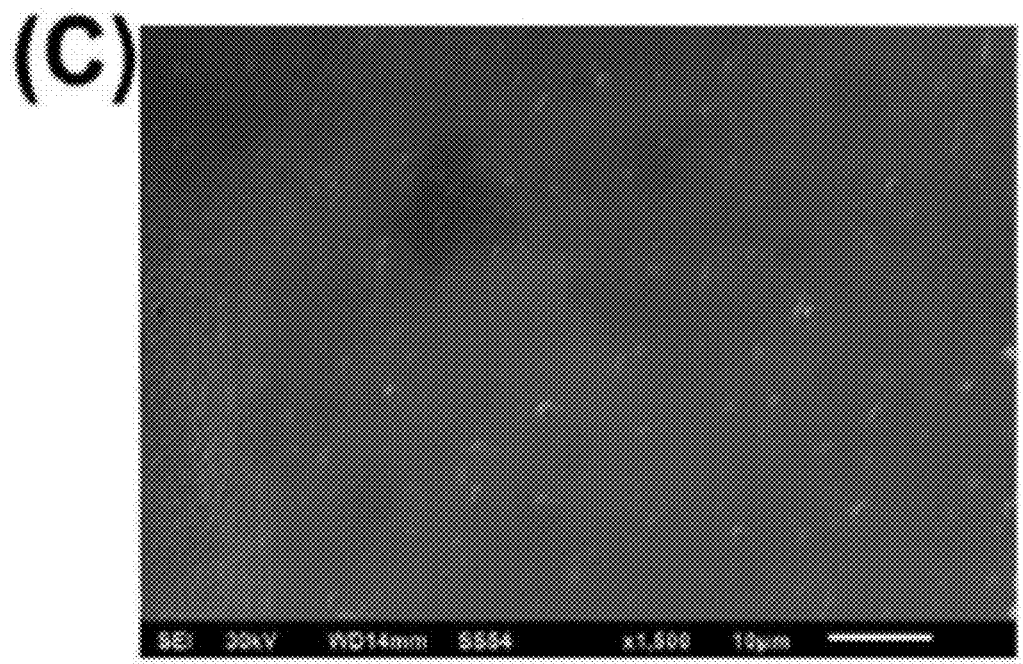
FIG. 13(A-C) illustrate digital image of a free-standing polyelectrolyte/(TMV-wt/TMV-lys)50 film in potassium phosphate buffer (0.1 mg/mL, pH 5.0). SEM micrographs of the released free-standing polyelectrolyte film with 50 bilayers of TMV-i488 and TMV-lys (B) and the polyelectrolyte film (C).

Preparation of Free-Standing Biofilms of Fluorescent Layer-by-Layer Assembled Plant Virus Nanoparticles Various strategies allow electrostatic LbL film assemblies to be released as a freely standing membrane. The most prominent techniques involve the assembly of the film on highly hydrophobic solid supports like Teflon, substrates that can be etched or dissolved after the LbL process, the direct construction of the multilayer assembly on TEM grids, and even through electrochemical stimulation. Here, the use of a sacrificial undercoat layer prior to the build up of the LbL virus assemblies was employed. Instead of pre-functionalizing the solid substrate with a self-assembled monolayer, the glass substrate was pre-coated with a thick layer of cellulose acetate (CA), which is soluble in acetone but not in aqueous systems. Since CA is negatively charged, the LbL deposition proceeded successfully. Before the assembly of the virus films, 50 bilayers of PDADMAC and PSS were initially deposited on top of the CA layer in order to provide a strong mechanical support for the TMV nanoparticles. Then, the polyelectrolyte/CA-modified glass was spun-coated with alternating solutions of TMV-wt and TMV-lys for 50 times. Since TMV-wt has been proven resilient in organic solvents such as acetone, the substrate with the sacrificial layer, polyelectrolyte and multilayers of TMV-wt and TMV-lys were submerged in acetone where the freely standing membrane can be peeled off from the solid support. FIG. 13A shows a digital image of the freely standing multilayer TMV assembly, which was stored in potassium phosphate buffer. The morphology of the free-standing films with (FIG. 13B) and without virus nanoparticles (FIG. 13C), were characterized using scanning electron microscopy (SEM). The surface morphology of the released film with TMV-wt and TMV-lys showed much rougher features with a dense amount of attached particles as compared to the free-standing film composed only of polyelectrolytes. Comparing the micrographs reveal that the virus nanoparticles remain intact and attached onto the polyelectrolyte membrane even after a year of immersion in potassium phosphate buffer.

Figure 14A:
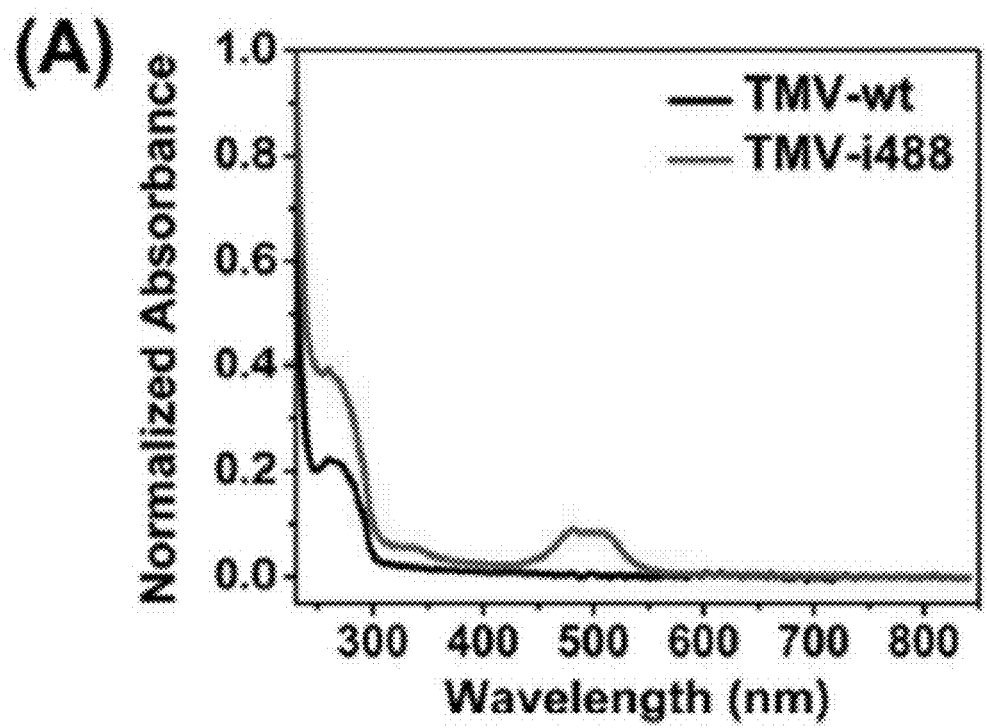
FIGS. 14(A-B) illustrate (A) UV-Vis absorbance spectra of TMV-wt and TMV-i488. (B) SDS-PAGE gel analysis of TMV-wt, TMV-lys, and TMV-i488 in UV light and after staining with Coomassie Blue.
Figure 14B:
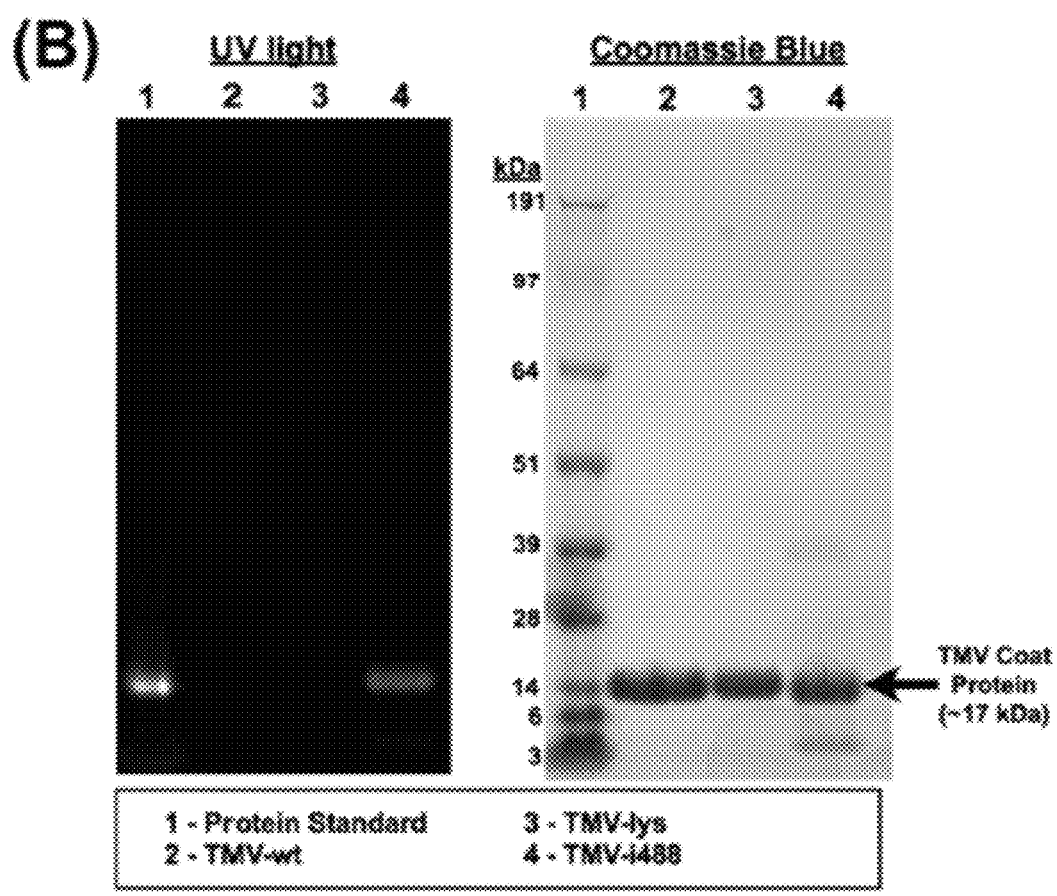
Figure 15:
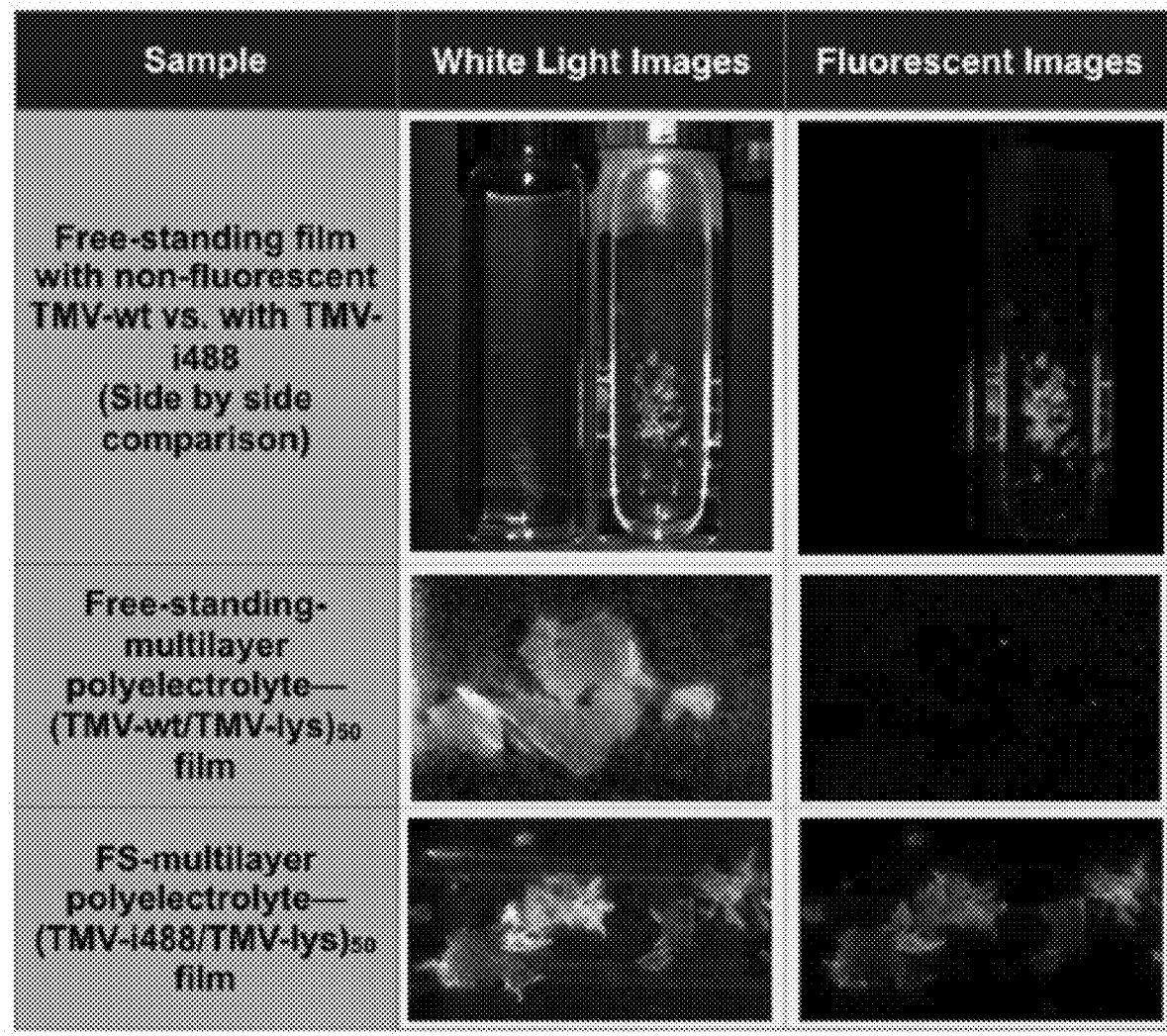
FIG. 15 illustrates fluorescence images of the membrane composed of polyelectrolyte and 50 bilayers of TMV-wt and TMV-lys and the polyelectrolyte film with 50 bilayers of TMVi488 and TMV-lys.

To demonstrate potential applications of the virus assemblies as cargo containers, the TMV-wt was covalently functionalized with Alexa Fluor 488 dye by click chemistry and was used to replace TMV-wt in fabricating the free-standing membranes of multi-layered virus nanoparticles. The emergence of the broad peak between 425 and 565 nm in the UV-Vis absorbance spectra (FIG. 14A) of the dye-modified TMV, which is denoted as TMV-i488, verifies the successful tethering of dye molecules onto the virus capsid. The particles were further characterized using SDS-PAGE to verify the purity and covalent modification of the coat proteins. TMV is composed of 2130 identical copies of a coat protein with a molecular weight of approximately 17 kDa; SDS-PAGE analysis confirmed fluorescence of the 488-labeled coat proteins when visualized under UV light, suggesting the successful conjugation of the Alexa dye. Staining the gel with Coomassie blue revealed the single band corresponding to the TMV coat protein at ~17 kDa for all types of virus nanoparticles. Using a Maestro fluorescence imaging system, a free-standing film built from the alternating depositions of TMV-i488 and TMV-Lys was analysed and compared against a film composed of TMV-wt and TMV-Lys. Based on the tabulated white light and fluorescent images in FIG. 15, only the film with TMV-i488 demonstrated fluorescence through a 560 nm long pass emission filter. These films remained mechanically robust and the fluorescence is still stable even after a year in storage in potassium phosphate buffer. This result suggests that a model dye molecule can indeed be stored within the multilayer virus assemblies by covalent attachment. For future work, other mechanisms of encapsulation such as electrostatic interactions and complexation can be also pursued as applied in area including the delivery and controlled release of drugs or therapeutic agents.

We demonstrated that 3-dimensional, multilayer virus scaffolds can be constructed through the alternating layer-by-layer deposition of wild-type TMV with a mutant TMV with genetically engineered lysine residues in the capsid protein. Replacing the threonine residues at the amino acid position 158 with lysine functional groups increased the overall negatively charged TMV particle surface to a more positive macromolecule. This resulted in a significant disparity in zeta potential measurements of the particles and became the driving force in the electrostatic layer-by-layer assembly of the particles on a solid support. The sequential build-up of the TMV-wt and TMV-lysine bilayers was monitored and investigated in detail through the resonant frequency and motional resistance shifts of a quartz crystal microbalance. Tapping-mode atomic force microscopy (AFM) was able to characterize the significant changes and stacking of the TMV-based particles on the surface. The protocol utilizing the electrostatic assembly of oppositely charged virus nanoparticles enabled the fast and steady build-up of rod-shaped TMV particles as opposed to using multiple bilayers of polyelectrolytes. Unlike the polyelectrolyte system, a more-positively charged TMV-lys is sufficiently large to act like spacer between negatively charged TMV particles.

The resulting multilayer constructs are reminiscent of the fibrous morphology of the extra-cellular morphologies. We also investigated whether the multilayer TMV scaffolds can demonstrate cell adhesion. As compared to the control systems of blank and polyelectrolyte-modified gold substrates, 0.5, 1, 4.5, and 5 bilayers of TMV-wt-TMV-lys biofilms supported the adhesion of 81±5, 95±10, 104±9, and 112±6 NIH-3T3 fibroblasts vells/mm$^2$ respectively. We noted that cell attachment increased with increasing layer deposition, the increased complexity of the assembly most likely mimics the natural tissue most realistically. In fact previous reports also indicated that cell attachment increased with increased viral layering.

Lastly, we also extended the LbL protocol to create freely standing multilayer virus membranes. Using a cellulose acetate (CA) undercoat layer, we increased the number of the polyelectrolyte and virus bilayers to achieve sufficient mechanical strength to be released in acetone where CA is soluble. Incorporating TMV in a free-standing biomembrane can open possible applications for drug delivery or vaccine nanopatches. For example, we recently demonstrated the use of TMV-wt as a drug delivery vehicle. We also reported the use of virus-like particles (VLPs) as in situ vaccines for tumor therapy. Towards these potential applications, we functionalized TMV-wt with a fluorescent dye, as proof-of-concept, and incorporated the functionalized TMV nanoparticle into the LbL process. Imaging confirmed that the assembly of a functional, fluorescent self-sustaining biomembrane. Since layer-by-layer works well even in highly complex solid supports and interfaces, the resulting multilayer viral scaffolds can prove to be a unique platform in developing materials for regenerative medicine or next-generation therapeutics for drug delivery or vaccine applications targeting cancer, cardiovascular disease or infectious diseases.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A nanoparticle construct for in situ delivery of plant virus or plant virus-like particles to a cell or tissue of interest of a subject, the nanoparticle construct comprising:
   a plurality of plant virus or plant virus-like particles, wherein the plant virus or plant virus-like particle is a rod-shaped virus particle, a plant picornavirus, or a filamentous plant virus or plant virus-like particle; and
   a plurality of dendrimers electrostatically coupled to the plant virus or plant virus-like particles, the nanoparticle construct upon in situ delivery to a subject providing a sustained release of the plant virus or plant virus-like particles and/or dendrimers to the cell or tissue.

2. The nanoparticle construct of claim 1, having a hydrodynamic radius of about 100 nm to about two microns.

3. The nanoparticle construct of claim 1, upon administration to a subject disassembling in a sustained manner at physiological salt concentrations.

4. The nanoparticle construct of claim 1, wherein the plant virus or virus-like particle is of the Secoviridae family or Alphafexiviridae family.

5. The nanoparticle construct of claim 1, wherein the plant virus or virus-like particle is a cowpea mosaic virus-like particle or potato virus X virus-like particle.

6. The nanoparticle construct of claim 1, wherein the rod-shaped virus is a tobacco mosaic virus.

7. The nanoparticle construct of claim 1, wherein the dendrimer is a G3-G10 dendrimer.

8. The nanoparticle construct of claim 1, comprising alternating electrostatically coupled layers of the plant virus or virus-like particles and the dendrimers.

9. The nanoparticle construct of claim 1, wherein the plant virus or virus-like particle is loaded with or bonded to a cargo molecule.

10. The nanoparticle construct of claim 9, wherein the cargo molecule is an anticancer agent.

* * * * *